US008795762B2

(12) United States Patent
Fulton et al.

(10) Patent No.: US 8,795,762 B2
(45) Date of Patent: Aug. 5, 2014

(54) SYSTEM AND METHOD FOR ENHANCED ELECTROSTATIC DEPOSITION AND SURFACE COATINGS

(75) Inventors: John L. Fulton, Richland, WA (US); George S. Deverman, Richland, WA (US); Dean W. Matson, Kennewick, WA (US); Clement R. Yonker, Kennewick, WA (US); C. Douglas Taylor, Franklin, NC (US); James B. McClain, Raleigh, NC (US); Joseph M. Crowley, Cambria, CA (US)

(73) Assignee: Battelle Memorial Institute, Richland, WA (US)

( * ) Notice: Subject to any disclaimer, the term of this patent is extended or adjusted under 35 U.S.C. 154(b) by 963 days.

(21) Appl. No.: 12/748,134

(22) Filed: Mar. 26, 2010

(65) Prior Publication Data

US 2011/0238161 A1 Sep. 29, 2011

(51) Int. Cl.
*B05D 1/04* (2006.01)
*B05D 7/14* (2006.01)
*A61F 2/06* (2013.01)

(52) U.S. Cl.
USPC .......... 427/2.24; 427/2.1; 427/2.25; 427/458; 427/475; 427/486

(58) Field of Classification Search
None
See application file for complete search history.

(56) References Cited

U.S. PATENT DOCUMENTS

| | | | |
|---|---|---|---|
| 3,087,860 | A | 4/1963 | Endicott |
| 3,123,077 | A | 3/1964 | Alcamo |
| 3,457,280 | A | 7/1969 | Schmitt et al. |
| 3,597,449 | A | 8/1971 | Deprospero et al. |
| 3,929,992 | A | 12/1975 | Sehgal et al. |
| 4,000,137 | A | 12/1976 | Dvonch et al. |
| 4,285,987 | A | 8/1981 | Ayer et al. |
| 4,326,532 | A | 4/1982 | Hammar |
| 4,336,381 | A | 6/1982 | Nagata et al. |
| 4,582,731 | A | 4/1986 | Smith |
| 4,655,771 | A | 4/1987 | Wallsten |
| 4,733,665 | A | 3/1988 | Palmaz |
| 4,734,227 | A | 3/1988 | Smith |
| 4,734,451 | A | 3/1988 | Smith |
| 4,931,037 | A | 6/1990 | Wetterman |
| 4,950,239 | A | 8/1990 | Gahara |
| 4,985,625 | A | 1/1991 | Hurst |
| 5,000,519 | A | 3/1991 | Moore |
| 5,090,419 | A | 2/1992 | Palestrant |
| 5,096,848 | A | 3/1992 | Kawamura |

(Continued)

FOREIGN PATENT DOCUMENTS

| | | |
|---|---|---|
| CA | 2589761 | 12/2004 |
| CN | 1465410 | 1/2004 |

(Continued)

OTHER PUBLICATIONS

PCT/US2011/032371, International Search Report dated Jul. 7, 2011.

(Continued)

*Primary Examiner* — Cachet Sellman
(74) *Attorney, Agent, or Firm* — Wilson, Sonsini, Goodrich & Rosati

(57) ABSTRACT

This disclosure describes the application of a supplemental corona source to provide surface charge on submicrometer particles to enhance collection efficiency and micro-structural density during electrostatic collection.

32 Claims, 6 Drawing Sheets

(56) References Cited

U.S. PATENT DOCUMENTS 5,106,650 A 4/1992 Hoy et al.
5,158,986 A 10/1992 Cha et al.
5,195,969 A 3/1993 Wang et al.
5,243,023 A 9/1993 Dezern
5,270,086 A 12/1993 Hamlin
5,288,711 A 2/1994 Mitchell et al.
5,324,049 A 6/1994 Mistrater et al.
5,340,614 A 8/1994 Perman et al.
5,342,621 A 8/1994 Eury
5,350,361 A 9/1994 Tsukashima et al.
5,350,627 A 9/1994 Nemphos et al.
5,356,433 A 10/1994 Rowland et al.
5,366,504 A 11/1994 Andersen et al.
5,368,045 A 11/1994 Clement et al.
5,372,676 A 12/1994 Lowe
5,385,776 A 1/1995 Maxfield et al.
5,403,347 A 4/1995 Roby et al.
5,470,603 A 11/1995 Staniforth et al.
5,494,620 A 2/1996 Liu et al.
5,500,180 A 3/1996 Anderson et al.
5,556,383 A 9/1996 Wang et al.
5,562,922 A 10/1996 Lambert
5,569,463 A 10/1996 Helmus et al.
5,609,629 A 3/1997 Fearnot et al.
5,626,611 A 5/1997 Liu et al.
5,626,862 A 5/1997 Brem et al.
5,674,242 A 10/1997 Phan et al.
5,725,570 A 3/1998 Heath
5,800,511 A 9/1998 Mayer
5,811,032 A 9/1998 Kawai et al.
5,824,049 A 10/1998 Ragheb et al.
5,837,313 A 11/1998 Ding et al.
5,873,904 A 2/1999 Ragheb et al.
5,924,631 A * 7/1999 Rodrigues et al. ................ 239/3
5,948,020 A 9/1999 Yoon et al.
5,957,975 A 9/1999 Lafont et al.
6,013,855 A 1/2000 McPherson et al.
6,077,880 A 6/2000 Castillo et al.
6,129,755 A 10/2000 Mathis et al.
6,143,037 A 11/2000 Goldsten et al.
6,146,356 A 11/2000 Wang et al.
6,146,404 A 11/2000 Kim et al.
6,153,252 A 11/2000 Hossainy et al.
6,171,327 B1 1/2001 Daniel et al.
6,190,699 B1 2/2001 Luzzi et al.
6,206,914 B1 3/2001 Soykan et al.
6,231,600 B1 5/2001 Zhong et al.
6,245,104 B1 6/2001 Alt
6,248,127 B1 6/2001 Shah et al.
6,248,129 B1 6/2001 Froix
6,273,913 B1 8/2001 Wright et al.
6,284,758 B1 9/2001 Egi et al.
6,309,669 B1 10/2001 Setterstrom et al.
6,319,541 B1 11/2001 Pletcher et al.
6,342,062 B1 1/2002 Suon et al.
6,355,691 B1 3/2002 Goodman
6,358,556 B1 3/2002 Ding et al.
6,361,819 B1 3/2002 Tedeschi et al.
6,364,903 B2 4/2002 Tseng et al.
6,368,658 B1 4/2002 Schwartz et al.
6,372,246 B1 4/2002 Wei et al.
6,387,121 B1 5/2002 Alt
6,409,716 B1 6/2002 Sahatjian et al.
6,414,050 B1 7/2002 Howdle et al.
6,416,779 B1 7/2002 D-Augustine et al.
6,448,315 B1 9/2002 Lidgren et al.
6,461,644 B1 10/2002 Jackson et al.
6,495,163 B1 12/2002 Jordan
6,497,729 B1 12/2002 Moussy et al.
6,506,213 B1 1/2003 Mandel et al.
6,517,860 B1 2/2003 Rosser et al.
6,521,258 B1 2/2003 Mandel et al.
6,524,698 B1 2/2003 Schmoock
6,537,310 B1 3/2003 Palmaz et al.
6,541,033 B1 4/2003 Shah
6,572,813 B1 6/2003 Zhang et al.
6,610,013 B1 8/2003 Fenster et al.
6,627,246 B2 9/2003 Mehta et al.
6,649,627 B1 11/2003 Cecchi et al.
6,660,176 B2 12/2003 Tepper et al.
6,669,785 B2 12/2003 DeYoung et al.
6,669,980 B2 12/2003 Hanson et al.
6,670,407 B2 12/2003 Howdle et al.
6,682,757 B1 1/2004 Wright
6,706,283 B1 3/2004 Appel et al.
6,710,059 B1 3/2004 Labrie et al.
6,720,003 B2 4/2004 Cheng et al.
6,726,712 B1 4/2004 Raeder-Devens et al.
6,736,996 B1 5/2004 Carbonell et al.
6,743,505 B2 6/2004 Antal et al.
6,749,902 B2 * 6/2004 Yonker et al. ................ 427/458
6,755,871 B2 6/2004 Damaso et al.
6,756,084 B2 6/2004 Fulton et al.
6,767,558 B2 7/2004 Wang et al.
6,780,475 B2 8/2004 Fulton et al.
6,794,902 B2 9/2004 Becker et al.
6,815,218 B1 11/2004 Jacobsen et al.
6,837,611 B2 1/2005 Kuo et al.
6,838,089 B1 1/2005 Carlsson et al.
6,838,528 B2 1/2005 Zhou
6,858,598 B1 2/2005 McKearn et al.
6,860,123 B1 3/2005 Uhlin et al.
6,884,377 B1 4/2005 Burnham et al.
6,884,823 B1 4/2005 Pierick et al.
6,897,205 B2 5/2005 Beckert et al.
6,905,555 B2 6/2005 DeYoung et al.
6,908,624 B2 6/2005 Hossainy et al.
6,916,800 B2 7/2005 McKearn et al.
6,923,979 B2 * 8/2005 Fotland et al. ................ 424/439
6,939,569 B1 9/2005 Green et al.
6,973,718 B2 12/2005 Sheppard et al.
7,148,201 B2 12/2006 Stern et al.
7,152,452 B2 12/2006 Kokish
7,160,592 B2 1/2007 Rypacek et al.
7,163,715 B1 1/2007 Kramer
7,169,404 B2 1/2007 Hossainy et al.
7,171,255 B2 1/2007 Holupka et al.
7,201,750 B1 4/2007 Eggers et al.
7,201,940 B1 4/2007 Kramer
7,229,837 B2 6/2007 Chen
7,279,174 B2 10/2007 Pacetti et al.
7,282,020 B2 10/2007 Kaplan
7,308,748 B2 12/2007 Kokish
7,326,734 B2 2/2008 Zi et al.
7,378,105 B2 5/2008 Burke et al.
7,419,696 B2 9/2008 Berg et al.
7,429,378 B2 9/2008 Serhan et al.
7,444,162 B2 10/2008 Hassan
7,455,688 B2 11/2008 Furst et al.
7,456,151 B2 11/2008 Li et al.
7,462,593 B2 12/2008 Cuttitta et al.
7,485,113 B2 2/2009 Varner et al.
7,524,865 B2 4/2009 D'Amato et al.
7,537,610 B2 5/2009 Reiss
7,537,785 B2 5/2009 Loscalzo et al.
7,553,827 B2 6/2009 Attawia et al.
7,713,538 B2 5/2010 Lewis et al.
7,727,275 B2 6/2010 Betts et al.
7,763,277 B1 7/2010 Canham et al.
7,837,726 B2 11/2010 Von Oepen et al.
7,919,108 B2 4/2011 Rees et al.
7,972,661 B2 * 7/2011 Pui et al. ...................... 427/475
2001/0026804 A1 10/2001 Boutignon
2001/0034336 A1 10/2001 Shah et al.
2001/0049551 A1 12/2001 Tseng et al.
2002/0091433 A1 7/2002 Ding et al.
2002/0125860 A1 9/2002 Schworm et al.
2002/0133072 A1 9/2002 Wang et al.
2002/0144757 A1 10/2002 Craig et al.
2003/0001830 A1 1/2003 Wampler et al.
2003/0031699 A1 2/2003 Van Antwerp
2003/0077200 A1 4/2003 Craig et al.
2003/0088307 A1 5/2003 Shulze et al.
2003/0125800 A1 7/2003 Shulze et al.

(56) References Cited

U.S. PATENT DOCUMENTS

| | | | |
|---|---|---|---|
| 2003/0143315 A1 | 7/2003 | Pui et al. | |
| 2003/0170305 A1 | 9/2003 | O'Neil et al. | |
| 2003/0180376 A1 | 9/2003 | Dalal et al. | |
| 2003/0185964 A1 | 10/2003 | Weber et al. | |
| 2003/0204238 A1 | 10/2003 | Tedeschi | |
| 2003/0222017 A1 | 12/2003 | Fulton et al. | |
| 2003/0222018 A1 | 12/2003 | Yonker et al. | |
| 2003/0232014 A1 | 12/2003 | Burke et al. | |
| 2004/0013792 A1 | 1/2004 | Epstein et al. | |
| 2004/0044397 A1 | 3/2004 | Stinson | |
| 2004/0059290 A1 | 3/2004 | Palasis et al. | |
| 2004/0106982 A1 | 6/2004 | Jalisi | |
| 2004/0126542 A1 | 7/2004 | Fujiwara et al. | |
| 2004/0143317 A1 | 7/2004 | Stinson et al. | |
| 2004/0157789 A1 | 8/2004 | Geall | |
| 2004/0170685 A1 | 9/2004 | Carpenter et al. | |
| 2004/0193177 A1 | 9/2004 | Houghton et al. | |
| 2004/0193262 A1 | 9/2004 | Shadduck | |
| 2004/0220660 A1 | 11/2004 | Shanley et al. | |
| 2004/0224001 A1 | 11/2004 | Pacetti et al. | |
| 2004/0236416 A1 | 11/2004 | Falotico | |
| 2004/0260000 A1 | 12/2004 | Chaiko | |
| 2005/0003074 A1 | 1/2005 | Brown et al. | |
| 2005/0004661 A1 | 1/2005 | Lewis et al. | |
| 2005/0010275 A1 | 1/2005 | Sahatjian et al. | |
| 2005/0015046 A1 | 1/2005 | Weber et al. | |
| 2005/0019747 A1 | 1/2005 | Anderson et al. | |
| 2005/0038498 A1 | 2/2005 | Dubrow et al. | |
| 2005/0048121 A1 | 3/2005 | East et al. | |
| 2005/0049694 A1 | 3/2005 | Neary | |
| 2005/0069630 A1 | 3/2005 | Fox et al. | |
| 2005/0070990 A1 | 3/2005 | Stinson | |
| 2005/0079199 A1 | 4/2005 | Heruth et al. | |
| 2005/0079274 A1 | 4/2005 | Palasis et al. | |
| 2005/0084533 A1 | 4/2005 | Howdle et al. | |
| 2005/0131513 A1 | 6/2005 | Myers et al. | |
| 2005/0147734 A1 | 7/2005 | Seppala et al. | |
| 2005/0166841 A1 | 8/2005 | Robida | |
| 2005/0175772 A1 | 8/2005 | Worsham et al. | |
| 2005/0177223 A1 | 8/2005 | Palmaz | |
| 2005/0191491 A1 | 9/2005 | Wang et al. | |
| 2005/0196424 A1 | 9/2005 | Chappa | |
| 2005/0216075 A1 | 9/2005 | Wang et al. | |
| 2005/0238829 A1 | 10/2005 | Motherwell et al. | |
| 2005/0255327 A1 | 11/2005 | Chaney | |
| 2005/0260186 A1 | 11/2005 | Bookbinder et al. | |
| 2005/0268573 A1 | 12/2005 | Yan | |
| 2005/0288481 A1 | 12/2005 | Desnoyer et al. | |
| 2006/0001011 A1* | 1/2006 | Wilson et al. | 252/500 |
| 2006/0020325 A1 | 1/2006 | Burgermeister et al. | |
| 2006/0030652 A1 | 2/2006 | Adams et al. | |
| 2006/0089705 A1 | 4/2006 | Ding et al. | |
| 2006/0093771 A1 | 5/2006 | Rypacek et al. | |
| 2006/0094744 A1 | 5/2006 | Maryanoff et al. | |
| 2006/0116755 A1 | 6/2006 | Stinson | |
| 2006/0121089 A1 | 6/2006 | Michal et al. | |
| 2006/0134211 A1 | 6/2006 | Lien et al. | |
| 2006/0136041 A1 | 6/2006 | Schmid et al. | |
| 2006/0147698 A1 | 7/2006 | Carroll et al. | |
| 2006/0153729 A1 | 7/2006 | Stinson | |
| 2006/0160455 A1 | 7/2006 | Sugyo et al. | |
| 2006/0188547 A1 | 8/2006 | Bezwada | |
| 2006/0193886 A1 | 8/2006 | Owens et al. | |
| 2006/0193890 A1 | 8/2006 | Owens et al. | |
| 2006/0198868 A1 | 9/2006 | DeWitt et al. | |
| 2006/0210638 A1 | 9/2006 | Liversidge et al. | |
| 2006/0216324 A1 | 9/2006 | Stucke et al. | |
| 2006/0222756 A1 | 10/2006 | Davila et al. | |
| 2006/0228415 A1 | 10/2006 | Oberegger et al. | |
| 2006/0276877 A1 | 12/2006 | Owens et al. | |
| 2007/0009564 A1 | 1/2007 | McClain et al. | |
| 2007/0032864 A1 | 2/2007 | Furst et al. | |
| 2007/0059350 A1 | 3/2007 | Kennedy et al. | |
| 2007/0110888 A1 | 5/2007 | Radhakrishnan et al. | |
| 2007/0123973 A1 | 5/2007 | Roth et al. | |
| 2007/0123977 A1 | 5/2007 | Cottone et al. | |
| 2007/0128274 A1 | 6/2007 | Zhu et al. | |
| 2007/0154554 A1 | 7/2007 | Burgermeister et al. | |
| 2007/0196423 A1 | 8/2007 | Ruane et al. | |
| 2007/0198081 A1 | 8/2007 | Castro et al. | |
| 2007/0203569 A1 | 8/2007 | Burgermeister et al. | |
| 2007/0259017 A1 | 11/2007 | Francis | |
| 2008/0051866 A1 | 2/2008 | Chen et al. | |
| 2008/0071359 A1 | 3/2008 | Thornton et al. | |
| 2008/0075753 A1 | 3/2008 | Chappa | |
| 2008/0095919 A1 | 4/2008 | McClain et al. | |
| 2008/0097575 A1 | 4/2008 | Cottone | |
| 2008/0097591 A1 | 4/2008 | Savage et al. | |
| 2008/0107702 A1 | 5/2008 | Jennissen | |
| 2008/0118543 A1 | 5/2008 | Pacetti et al. | |
| 2008/0124372 A1 | 5/2008 | Hossainy et al. | |
| 2008/0138375 A1 | 6/2008 | Yan et al. | |
| 2008/0206304 A1 | 8/2008 | Lindquist et al. | |
| 2008/0213464 A1 | 9/2008 | O'Connor | |
| 2008/0255510 A1 | 10/2008 | Wang | |
| 2008/0292776 A1 | 11/2008 | Dias et al. | |
| 2008/0300669 A1 | 12/2008 | Hossainy | |
| 2009/0043379 A1 | 2/2009 | Prescott | |
| 2009/0062909 A1 | 3/2009 | Taylor et al. | |
| 2009/0068266 A1 | 3/2009 | Raheja et al. | |
| 2009/0076446 A1 | 3/2009 | Dubuclet et al. | |
| 2009/0082855 A1 | 3/2009 | Borges et al. | |
| 2009/0105809 A1 | 4/2009 | Lee et al. | |
| 2009/0110711 A1 | 4/2009 | Trollsas et al. | |
| 2009/0111787 A1 | 4/2009 | Lim et al. | |
| 2009/0123515 A1 | 5/2009 | Taylor et al. | |
| 2009/0186069 A1 | 7/2009 | DeYoung et al. | |
| 2009/0202609 A1 | 8/2009 | Keough et al. | |
| 2009/0216317 A1 | 8/2009 | Cromack et al. | |
| 2009/0227949 A1 | 9/2009 | Freyman et al. | |
| 2009/0231578 A1 | 9/2009 | Ling et al. | |
| 2009/0263460 A1 | 10/2009 | McDonald | |
| 2009/0285974 A1 | 11/2009 | Kerrigan | |
| 2009/0292351 A1 | 11/2009 | McClain et al. | |
| 2009/0297578 A1 | 12/2009 | Trollsas et al. | |
| 2010/0015200 A1 | 1/2010 | McClain et al. | |
| 2010/0030261 A1 | 2/2010 | McClain et al. | |
| 2010/0042206 A1 | 2/2010 | Yadav et al. | |
| 2010/0063570 A1 | 3/2010 | Pacetti et al. | |
| 2010/0063580 A1 | 3/2010 | McClain et al. | |
| 2010/0074934 A1 | 3/2010 | Hunter | |
| 2010/0155496 A1* | 6/2010 | Stark et al. | 239/3 |
| 2010/0166869 A1 | 7/2010 | Desai et al. | |
| 2010/0196482 A1 | 8/2010 | Radovic-Moreno et al. | |
| 2010/0198330 A1 | 8/2010 | Hossainy et al. | |
| 2010/0211164 A1 | 8/2010 | McClain et al. | |
| 2010/0228348 A1 | 9/2010 | McClain et al. | |
| 2010/0239635 A1 | 9/2010 | McClain et al. | |
| 2010/0241220 A1 | 9/2010 | McClain et al. | |
| 2010/0256746 A1 | 10/2010 | Taylor et al. | |
| 2010/0256748 A1 | 10/2010 | Taylor et al. | |
| 2010/0272778 A1 | 10/2010 | McClain et al. | |
| 2010/0298928 A1 | 11/2010 | McClain et al. | |
| 2011/0009953 A1 | 1/2011 | Luk et al. | |
| 2011/0159069 A1 | 6/2011 | Shaw et al. | |
| 2011/0190864 A1 | 8/2011 | McClain et al. | |
| 2011/0238161 A1 | 9/2011 | Fulton et al. | |
| 2011/0257732 A1 | 10/2011 | McClain et al. | |
| 2011/0264190 A1 | 10/2011 | McClain et al. | |
| 2012/0064124 A1 | 3/2012 | McClain et al. | |
| 2012/0172787 A1 | 7/2012 | McClain et al. | |
| 2012/0177742 A1 | 7/2012 | McClain et al. | |
| 2012/0323311 A1 | 12/2012 | McClain et al. | |

FOREIGN PATENT DOCUMENTS

| | | |
|---|---|---|
| EP | 0604022 | 6/1994 |
| EP | 0982041 | 3/2000 |
| EP | 1195822 A2 | 4/2002 |
| EP | 1454677 | 9/2004 |
| EP | 2197070 A1 | 6/2010 |
| EP | 2293357 A1 | 3/2011 |
| EP | 2293366 A1 | 3/2011 |
| JP | 1994-098902 | 4/1994 |

(56) References Cited

FOREIGN PATENT DOCUMENTS

| | | | |
|---|---|---|---|
| JP | H09-056807 | | 3/1997 |
| JP | 2003-205037 | | 7/2003 |
| JP | 2003-533493 | | 11/2003 |
| JP | 2003533492 | | 11/2003 |
| JP | 2004/173770 | | 6/2004 |
| JP | 2004-518458 | | 6/2004 |
| JP | 2004-529674 | | 9/2004 |
| JP | 2005-523119 | | 8/2005 |
| JP | 2005-523332 | | 8/2005 |
| JP | 2005-296690 | | 10/2005 |
| JP | 2009-501566 | | 1/2009 |
| WO | WO 96/20698 | | 7/1996 |
| WO | WO 97/45502 | | 12/1997 |
| WO | WO-01/54662 | | 8/2001 |
| WO | WO-01-87371 | | 11/2001 |
| WO | WO-01/87372 | | 11/2001 |
| WO | WO-02/40702 | | 5/2002 |
| WO | WO-02/090085 | | 11/2002 |
| WO | WO-03/039553 | | 5/2003 |
| WO | WO-03/101624 | A1 | 12/2003 |
| WO | WO-2004/028589 | | 4/2004 |
| WO | WO-2004/098574 | | 11/2004 |
| WO | WO-2005/042623 | A1 | 5/2005 |
| WO | WO-2005/063319 | | 7/2005 |
| WO | WO-2005/069889 | | 8/2005 |
| WO | WO-2005/117942 | A2 | 12/2005 |
| WO | WO-2006/052575 | | 5/2006 |
| WO | WO-2006/065685 | | 6/2006 |
| WO | WO-2006/083796 | A2 | 8/2006 |
| WO | WO-2006/099276 | A2 | 9/2006 |
| WO | 2007011707 | A2 | 1/2007 |
| WO | WO-2007-002238 | | 1/2007 |
| WO | WO-2007/011707 | A2 | 1/2007 |
| WO | WO-2007/011707 | A3 | 1/2007 |
| WO | WO-2007/011708 | A2 | 1/2007 |
| WO | WO-2007/011708 | A3 | 1/2007 |
| WO | WO-2007/092179 | | 8/2007 |
| WO | WO-2007/127363 | A2 | 11/2007 |
| WO | WO 2007/143609 | | 12/2007 |
| WO | WO-2008/042909 | | 4/2008 |
| WO | WO-2008/046641 | | 4/2008 |
| WO | WO-2008/046642 | | 4/2008 |
| WO | WO-2008/052000 | | 5/2008 |
| WO | WO-2008/086369 | | 7/2008 |
| WO | WO 2008/086369 | | 7/2008 |
| WO | WO-2008/131131 | A1 | 10/2008 |
| WO | WO-2008/148013 | | 12/2008 |
| WO | WO-2009/146209 | | 12/2009 |
| WO | WO-2010/009335 | | 1/2010 |
| WO | WO 2010/009335 | | 1/2010 |
| WO | WO-2010/075590 | | 7/2010 |
| WO | WO-2010/111196 | A2 | 9/2010 |
| WO | WO-2010/111196 | A3 | 9/2010 |
| WO | WO-2010/111232 | A3 | 9/2010 |
| WO | WO-2010/111232 | A9 | 9/2010 |
| WO | WO-2010/111238 | A2 | 9/2010 |
| WO | WO-2010/111238 | A3 | 9/2010 |
| WO | WO-2010/120552 | A2 | 10/2010 |
| WO | WO-2010/120552 | A3 | 10/2010 |
| WO | WO-2010/121187 | A2 | 10/2010 |
| WO | WO-2010/121187 | A3 | 10/2010 |
| WO | WO-2011/009096 | A1 | 1/2011 |
| WO | WO-2011/097103 | | 8/2011 |
| WO | WO-2011/119762 | | 9/2011 |
| WO | WO-2011/130448 | | 10/2011 |
| WO | WO-2011/133655 | | 10/2011 |
| WO | WO-2012/009684 | | 1/2012 |
| WO | WO-2012/034079 | | 3/2012 |
| WO | WO-2012/092504 | | 7/2012 |
| WO | WO-2012/142319 | | 10/2012 |
| WO | WO-2012/166819 | | 12/2012 |

OTHER PUBLICATIONS

Hinds, William C., Aerosol Technology, Properties, Behavior and Measurement of Airborne Particles, Department of Environmental Health Sciences, Harvard University School of Public Health, Boston, Massachusetts, 1982, 283-314.

Fulton, John L. et al., Thin fluoropolymer films and nanoparticle coatings from the rapid expansion of supercritical carbon dioxide solutions with electrostatic collection, Polymer Communication, 2003, 2627-3632.

Electrostatic Process, Wiley Encyclopedia of Electrical and Electronics Engineering, vol. 7, John Wiley & Sons, Inc. , 1999, 15-39.

Poling, Bruce E., et al., The Properties of Gases and Liquids, Chapter 9, Viscosity, McGraw-Hill, 2001, 9.1-9.97.

CRC handbook of chemistry and physics. 71st ed. David R. Lide, Editor-in-Chief. Boca Raton, FL, CRC Press; 1990, 6-140.

Perry, Robert H. et al., Chemical Engineer's Handbook, 5th Edition, McGraw-Hill, New York, 1973, 20-106.

Akoh et al., "One-Stage Synthesis of Raffinose Fatty Acid Polyesters." Journal Food Science (1987) 52:1570.

Albert et al., "Antibiotics for preventing recurrent urinary tract infection in non-pregnant women," Cochrane Database System Rev. 3, CD001209 (2004).

Au et al., "Methods to improve efficacy of intravesical mitomycin C: Results of a randomized phase III trial," Journal of the National Cancer Institute, 93(8), 597-604 (2001).

AU2006270221 Exam Report dated Apr. 6, 2010.

AU2011232760 Exam Report dated Apr. 10, 2013.

AU2012203203 Exam Report dated Apr. 12, 2013.

AU2007243268 Exam Report dated May 15, 2013.

AU2007243268 Exam Report dated Aug. 31, 2011.

AU2009251504 Exam Report dated Dec. 8, 2011.

AU2009270849 Exam Report dated Feb. 14, 2012.

AU2012203577 Exam Report dated Jun. 7, 2013.

AU2011256902 Exam Report dated Jun. 13, 2013.

Balss et al., "Quantitative spatial distribution of sirolumus and polymers in drug-eluting stents using confocal Raman microscopy," J. of Biomedical Materials Research Part A, 258-270 (2007).

Belu et al., "Three-Dimensional Compositional Analysis of Drug Eluting Stent Coatings Using Cluster Secondary Ioan Mass Spectroscopy," Anal. Chem. 80:624-632 (2008).

Belu, et al., "Chemical imaging of drug eluting coatings: Combining surface analysis and confocal Rama microscopy" J. Controlled Release 126: 111-121 (2008).

Boneff, "Topical Treatment of Chronic Prostatitis and Premature Ejaculation," International Urology and Nephrology 4(2):183-186 (1971).

Bookbinder et al., "A recombinant human enzyme for enhanced interstitial transport of therapeutics," Journal of Controlled Release 114:230-241 (2006).

Borchert et al., "Prevention and treatement of urinary tract infection with probiotics: Review and research perspective," Indian Journal Urol. 24(2):139-144 (2008).

Brunstein et al., "Histamine, a vasoactive agent with vascular disrupting potential improves tumour response by enhancing local drug delivery," British Journal of Cancer 95:1663-1669 (2006).

Bugay et al., "Raman Analysis of Pharmaceuticals," in "Applications of Vibrational Spectroscopy in Pharmaceutical Research and Development," Ed. Pivonka, D.E., Chalmers, J.M., Griffiths, P.R. (2007) Wiley and Sons.

CA 2615452 Office Action dated Dec. 19, 2012.

CA 2684482 Office Action Jul. 11, 2012.

CA 2684482 Office Action dated Nov. 10, 2011.

CA 2688314 Office Action dated Jun. 6, 2012.

CA 2730995 Office Action dated Sep. 26, 2012.

CA 2757276 Office Action dated Feb. 15, 2013.

Ca 2756307 Office action dated Feb. 18, 2013.

CA 2756386 Office action dated Mar. 15, 2013.

CA 2759015 Office action dated Apr. 8, 2013.

CA 2756388 Office Action dated Apr. 11, 2013.

CA 2613280 Office Action dated Oct. 2, 2012.

CA 2667228 Office action dated May 7, 2013.

CA 2730995 Office action dated May 29, 2013.

CA 2650590 Office action dated Jul. 23, 2013.

Cadieux et al., "Use of triclosan-eluting ureteral stents in patients with long-term stents," J. Endourol (Epub) (Jun. 19, 2009).

(56) References Cited

OTHER PUBLICATIONS

Channon et al., "Nitric Oxide Synthase in Atherosclerosis and Vascular Injury: Insights from Experimental Gene Therapy," Arteriosclerosis, Thrombosis and Vascular Biology, 20(8):1873-1881 (2000).
Chen et al Immobilization of heparin on a silicone surface through a heterobifunctional PEG spacer. Biomaterials. Dec. 2005;26(35):7418-24.
Chlopek et al. "The influence of carbon fibres on the resorption time and mechanical properties of the lactide—glycolide co-polymer." J. Biomater. Sci. Polymer Edn, vol. 18, No. 11, pp. 1355-1368 (2007).
Clair and Burks, "Thermoplastic/Melt-Processable Polyimides," NASA Conf. Pub. #2334 (1984), pp. 337-355.
CN 2006800258093 Office Action dated May 30, 2012.
CN 200880007308.1 Office Action dated Nov. 23, 2011.
CN 200880007308.1 Office Action dated Oct. 18, 2012.
CN 200880020515 Office Action dated Oct. 9, 2012.
CN 200880100102.3 Office Action dated Jun. 1, 2012.
CN 200980122691 Office Action dated Oct. 10, 2012.
CN 200780047425.6 Office action dated Aug. 3, 2012.
CN 200780047425.6 Office action dated Feb. 28, 2013.
CN 200980136432.2 Office action dated Jan. 14, 2013.
CN 200880100102.3 Office Action dated Apr. 11, 2013.
CN 200880007308.1 Office Action dated Jul. 3, 2013.
CN 200880020515 Office Action dated Jul. 22, 2013.
Cohen, et al. "Sintering Technique for the Preparation of Polymer Matrices fro the Controlled Release of Macromolecules." Journal of Pharamceutical Sciences, vol. 73, No. 8, 1984, p. 1034-1037.
CRC Handbook of chemistry and physics. 71st ed. David R. Lide, Editor-in-Chief. Boca Raton, FL, CRC Press; 1990; 6-140.
Cyrus et al., "Intramural delivery of rapamycin with alphavbeta3-targeted paramagnetic nanoparticles inhibits stenosis after balloon injury," Arterioscler Thromb Vasc Biol 2008;28:820-826.
Derwent-Acc-No. 2004-108578 Abstracting 2004003077; Jan. 8, 2004; 3 pages.
DiStasi et al., "Percutaneous sequential bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides." J. Polym Sci. 25:3373-3386 (1987).
Domingo, C. et al., "Precipication of ultrafine organic crystals from the rapid expansion of supercritical solutions over a capillary and a frit nozzle," J. Supercritical Fluids 10:39-55 (1997).
Dzik-Jurasz, "Molecular imaging in vivo: an introduction," The British Journal of Radiology, 76:S98-S109 (2003).
EA 201001497 Office Action dated Feb. 11, 2013 (no translation).
EA 200901254/28 Office Action dated Jul. 18, 2012.
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacol 74(6):1587-1598 (2008).
EP06773731.2 Search Report dated Oct. 2, 2012.
EP06787258.0 Search Report dated Feb. 6, 2012.
EP07756094.4 Search Report dated Aug. 31, 2012.
EP08733210.2 Search Report dated Oct. 23, 2012.
EP08756215.3 Search Report dated Oct. 5, 2011.
EP08756215.3 Search Report dated Jan. 28, 2013.
EP09805981.9 Office Action dated Feb. 13, 2013.
EP06787258.0 Office Action dated Mar. 15, 2013.
EP09755571.8 Search Report dated Apr. 9, 2013.
EP08705772.5 Search Report dated Feb. 20, 2013.
EP07756094.4 Office action dated May 29, 2013.
EP08733210.2 Office action dated Jul. 16, 2013.
EP11769546.0 Search Report dated Sep. 19, 2013.
EP09798764.8 Search Report dated Sep. 30, 2013.
Ettmayer et al. Lessons learned from marketed and investigational prodrugs. J Med Chem. May 6, 2004;47(10):2393-404.
Fibbi et al., "Chronic inflammation in the pathogenesis of benign prostatic hyperplasia," Int J Androl. Jun. 1, 2010;33(3):475-88.
Fleischmann et al., "High Expression of Gastrin-Releasing Peptide Receptors in the Vascular bed of Urinary Tract Cancers: Promising Candidates for Vascular Targeting Applications." Jun. 2009, Endocr. Relat. Cancer 16(2):623-33.
Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury," Oct. 29, 2008, NeuroReport 19(16):1585-1588.
Fulton et al. Thin Fluoropolymer films and nanoparticle coatings from the rapid expansion of supercritical carbon dioxide solutions with electrostatic collection, Polymer Communication. 2003; 2627-3632.
Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Differential effects of Drug-Eluting Stents on Local Endothelium-Dependent Coronary Vasomotion." JACC vol. 51, No. 22, 2008, Endothelium and DES Jun. 3, 2008:2123-9.
Hartmann et al., "Tubo-ovarian abscess in virginal adolescents: exposure of the underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44 (2003) 2933-2937.
Hinds, WC. Aerosol Technology, Properties, Behavior and Measurement of Airborne Particles, Department of Environmental Health Sciences, Harvard University School of Public Health, Boston, Massachusetts. 1982; 283-314.
Hladik et al., "Can a topical microbicide prevent rectal HIV transmission?" PLoS Med. 5(8):e167 (2008).
Iconomidou et al., "Secondary Structure of Chorion Proteins of the Teleosatan Fish Dentex dentex by ATR FR-IR and FT-Raman Spectroscopy," J. of Structural Biology, 132, 112-122 (2000).
IN-368/DELNP/2008 Exam Report dated Oct. 17, 2011.
IL-208648 Official Notification dated Feb. 9, 2012.
Jackson et al., "Characterization of perivascular poly(lactic-co-glycolic acid) films containing paclitaxel" *Int. J. of Pharmaceutics*, 283:97-109 (2004), incorporated in its entirety herein by reference.
Jensen et al., Neointimal hyperplasia after sirollmus-eluting and paclitaxel-eluting stend implantation in diabetic patients: the randomized diabetes and drug eluting stent (DiabeDES) intravascular ultrasound trial. European heart journal (29), pp. 2733-2741. Oct. 2, 2008. Retrieved from the Internet. Retrieved on [Jul. 17, 2012]. URL:<http://eurheartj.oxfordjournals.org/content/29/22/2733.full.pdf> entire document.
Jewell, et al., "Release of Plasmid DNA from Intravascular Stents Coated with Ultrathin Multilayered Polyelectrolyte Films" *Biomacromolecules*. 7: 2483-2491 (2006).
Johns, H.E, J.R.Cunningham, Thomas, Charles C., Publisher, "The Physics of Radiology, "1983, Springfield, IL, pp. 133-143.
Joner et al. "Site-specific targeting of nanoparticle prednisolone reduces in-stent restenosis in a rabbit model of established atheroma," Arterioscler Thromb Vasc Biol. 2008;28:1960-1966.
Mei et al., "Local Delivery of Modified Paclitaxel-Loaded Poly( ϵ-caprolactone)/Pluronic F68 Nanoparticles for Long-Term Inhibition of Hyperplasia," Journal of Pharmaceutical Sciences, Vol. 98, No. 6, June 2009.
Jovanovic et al. "Stabilization of Proteins in Dry Powder Formulations Using Supercritical Fluid Technology," Pharm. Res. 2004; 21(11).
JP 2008-521633 Office Action dated Oct. 12, 2012.
JP2008-521633 Office Action dated Dec. 28, 2011 .
JP-2009-534823 Office Action dated Sep. 20, 2012.
JP-2009-534823 Office Action dated Feb. 21, 2012.
JP-2009-545647 Office Action dated Jun. 5, 2012.
JP-2010-504253 Office Action dated Dec. 12, 2011.
JP-2010-504253 Office Action dated Dec. 7, 2012.
JP-2011-518920 Office action dated Dec. 17, 2012.

(56) References Cited

OTHER PUBLICATIONS

JP-2009-534823 Office Action dated Apr. 23, 2013.
JP-2012-503677 Office action dated Jan. 18, 2013.
JP-2011-505248 Office action dated Jun. 4, 2013.
JP-2010-510441 Office action dated May 7, 2013.
JP-2009-545647 Office Action dated May 14, 2013.
Kazemi et al., "The effect of betamethasone gel in reducing sore throat, cough, and hoarseness after laryngo-tracheal intubation," Middle East J. Anesthesiol. 19(1):197-204 (2007).
Kehinde et al., "Bacteriology of urinary tract infection associated with indwelling J ureteral stents," J. Endourol. 18(9):891-896 (2004).
Kelly et al., "Double-balloon trapping technique for embolization of a large wide-necked superior cerebellar artery aneurysm: case report," Neurosurgery 63(4 Suppl 2):291-292 (2008).
Khan et al., "Cyclic Acetals of 4,1',6'-Trichloro-4,1',6',-Trideoxy-Trideoxy-galacto-Sucrose and their Conversion into Methyl Ether Derivatives.". Carb. Res. (1990) 198:275-283.
Khan et al., "Chemistry and the new uses of Sucrose: How Important?" Pur and Appl. Chem (1984) 56:833-844.
Khan et al., "Enzymic Regioselective Hydrolysis of Peracetylated Reducing Disaccharides, Specifically at the Anomeric Centre: Intermediates for the Synthesis of Oligosaccharides." Tetrahedron Letters (1933) 34:7767.
Khayankarn et al., "Adhesion and Permeability of Polyimide-Clay Nanocomposite Films for Protective Coatings," Journal of Applied Polymer Science, vol. 89, 2875-2881 (2003).
Koh et al. "A novel nanostructured poly(lactic-co-glycolic-acid)—multi-walled carbon nanotube composite for blood-contacting applications: Thrombogenicity studies." Acta Biomaterialia 5 (2009): 3411-3422.
KR10-2008-7003756 Office Action dated Oct. 30, 2012.
KR10-2008-7003756 Office Action dated Sep. 23, 2013 (no translation).
Kurt et al., "Tandem oral, rectal and nasal administrations of Ankaferd Blood Stopper to control profuse bleeding leading to hemodynamic instability," Am J. Emerg. Med. 27(5):631, e1-2 (2009).
Labhasetwar et al., "Arterial uptake of biodegradable nanoparticles: effect of surface modifications," Journal of Pharmaceutical Sciences, vol. 87, No. 10, Oct. 1998; 1229-1234.
Lamm et al., "Bladder Cancer: Current Optimal Intravesical Treatment: Pharmacologic Treatment," Urologic Nursing 25(5):323-6, 331-2 (Oct. 26, 2005).
Latella et al., "Nanoindentation hardness. Young's modulus, and creep behavior of organic-inorganic silica-based sol-gel thin films on copper," J Mater Res 23(9): 2357-2365 (2008).
Lawrence et al., "Rectal tacrolimus in the treatment of resistant ulcerative proctitis," Aliment. Pharmacol Ther. 28(10):1214-20 (2008).
Lee et al., "Novel therapy for hearing loss: delivery of insulin-like growth factor 1 to the cochlea using gelatin hydrogel," Otol. Neurotol. 28(7):976-81 (2007).
Lehmann et al, "Drug treatment of nonviral sexually transmitted diseases: specific issues in adolescents," Pediatr Drugs 3(7):481-494 (2001).
Mahoney et al., "Three-Dimensional Compositional Analysis of Drug Eluting Stent Coatings Using Cluster Secondary Ion mass Spectrometry," Anal. Chem. , 80, 624-632 (2008).
Mario, C.D. et al., "Drug-Eluting Bioabsorbable Magnesium Stent," J. Interventional Cardiology 16(6):391-395 (2004).
McAlpine, J.B. et al., "Revised NMR Assignments for Rapamycine," J. Antibiotics 44:688-690 (1991).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Melonakos et al., Treatment of low-grade bulbar transitional cell carcinoma with urethral instillation of mitomycin C, Oct. 28, 2008, Adv. Urol., 173694 Epub.
Merrett et al., "Interaction of corneal cells with transforming growth factor beta2- modified poly dimethyl siloxane surfaces," Journal of Biomedical Materials Research, Part A, vol. 67A, No. 3, pp. 981-993 (2003).
Merriam-Webster Online Dictionary, obtained onlie at: http://www.merriam-webster.com/dictionary/derivative, downloaded Jan. 23, 2013.
Middleton and Tipton, Synthetic biodegradable polymers as orthopedic devises. Biomaterials 2000; 21:2335-46.
Minchin, "Nanomedicine: sizing up targets with nanoparticles," Nature Nanotechnology, vol. 33, Jan. 12-13, 2008.
Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion of Supercritical Solution with a Nonsolvent," AIChE J. 2000;46(4):857-65.
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence of tubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:targeting PARP-1 within the ischemic neurovaschular units as a realistic avenue to stroke treatment," FEBS J. 276(1):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
Murphy et al., "Chronic prostatitis: management strategies," Drugs 69(1): 71-84 (2009).
NZ 588549 Examination Report dated Mar. 28, 2011.
NZ 600814 Examination Report dated Jun. 29, 2012.
O'Neil et al., "Extracellular matrix binding mixed micelles for drug delivery applications," Journal of Controlled Release 137 (2009) 146-151.
O'Donnell et al., "Salvage intravesical therapy with interferon-alpha 2b plus low dose bacillus Calmette-Guerin alone perviously failed," Journ. Urology, 166(4):1300-1304 (2001).
Olbert et al., "In vitro and in vivo effects of CpG-Oligodeoxynucleotides (CpG-ODN) on murine transitional cell carcinoma and on the native murine urinary bladder wall," Anticancer Res. 29(6):2067-2076 (2009).
Ong and Serruys, "Technology Insight: an overview of research in drug-eluting stents," Nat. Clin. Parct. Cardiovas. Med. 2(12):647-658 (2005).
PCT/US06/24221 International Search Report mailed Jan. 29, 2007.
PCT/US06/27321 International Search Report mailed Oct. 16, 2007.
PCT/US06/27322 International Search Report mailed Apr. 25, 2007.
PCT/US07/10227 International Search Report mailed Aug. 8, 2008.
PCT/US07/80213 International Search Report mailed Apr. 16, 2008.
PCT/US07/82275 International Search Report mailed Apr. 18, 2008.
PCT/US08/11852 International Search Report mailed Dec. 19, 2008.
PCT/US08/50536 International Search Report mailed Jun. 2, 2008.
PCT/US08/60671 International Search Report mailed Sep. 5, 2008.
PCT/US08/64732 International Search Report mailed Sep. 4, 2008.
PCT/US09/41045 International Search Report mailed Aug. 11, 2009.
PCT/US09/50883 International Search Report mailed Nov. 17, 2009.
PCT/US12/46545 International Search Report mailed Nov. 20, 2012.
PCT/US12/50408 International Search Report mailed Oct. 19, 2012.
PCT/US2012/040040 International Search Report mailed Sep. 7, 2012.
Perry et al., Chemical Engineer's Handbook, 5th Edition, McGraw-Hill, New York, 1973; 20-106.
Torchlin, "Micellar Nanocarriers: Pharmaecutial Perspectives," Pharmaceutical Research, vol. 24, No. 1, Jan. 2007.
Plas et al., "Tubers and tumors: rapamycin therapy for benign and malignant tumors", Curr Opin Cell Bio 21: 230-236, (2009).
Poling et al., The Properties of Gases and Liquids. McGraw-Hill. 2001; 9:1-9.97.

(56) References Cited

OTHER PUBLICATIONS

Pontari, "Chronic prostatitis/chronic pelvic pain syndrome in elderly men: toward better understanding and treatment", Drugs Aging 20(15):1111-1115 (2003).
Pontari, "Inflammation and anti-inflammatory therapy in chronic prostatits," Urology 60(6Suppl):29-33 (2002).
Raganath et al., "Hydrogel matrix entrapping PLGA-paclitaxel microspheres: drug delivery with near zero-order release and implantability advantages for malignant brain tumour," Pharm Res (Epub) Jun. 20, 2009).
Ranade et al., "Physical characterization of controlled release of paclitaxel from the TAXUS Express2 drug-eluting stent," J. Biomed Mater. Res. 71(4):625-634 (2004).
Reddy et al., "Inhibition of apoptosis through localized delivery of rapamycin-loaded nanoparticles prevented neointimal hyperplasia and reendothelialized injured artery," Circ Cardiovasc Intery 2008;1;209-216.
Ristikankare et al., "Sedation, topical pharnygeal anesthesia and cardiorespiratory safety during gastroscopy," J. Clin Gastorenterol. 40(1):899-905 (2006).
Sahajanand Medical Technologies (Supralimus Core; Jul. 6, 2008).
Salo et al., "Bioflim formation by *Escherichia coli* isolated from patients with urinary tract infections," Clin Nephrol. 71(5):501-507 (2009).
Saxena et al., "Haemodialysis catheter-related bloodstream infections: current treatment options and strategies for prevention," Swiss Med Wkly 135:127-138 (2005).
Schetsky, L. McDonald, "Shape Memory Alloys", Encyclopedia of Chemical Technology (3d Ed), John Wiley & Sons 1982, vol. 20 pp. 726-736.
Scheuffler et al., "Crystal Structure of Human Bone Morphogenetic Protein-2 at 2.7 Angstrom resolution," Journal of Molecular Biology, vol. 287, Issue 1, Mar. 1999, retrieved online at http://www.sciencedirect.com/science/article/pii/S002283699925901.
Schmidt et al., "A Comparison of the Mechanical Performance Characteristics of Seven Drug-Eluting Stent Systems," Catheterization and Cardiovascular Interventions 73:350-360 (2009).
Schmidt et al., "In vitro measurement of quality parameters of stent-catheter systems," Biomed Techn 50(S1):1505-1506 (2005).
Schmidt et al., "New aspects of in vitro testing of arterial stents based on the new European standard," EN 14299, [online] (2009), [retrieved on Mar. 10, 2001] http://www.lib0ev.de/pl/pdf/EN14299.pdf (2009).
Schmidt et al., "Trackability, Crossability, and Pushability of Coronary Stent Systems-An Experimental Approach," Biomed Techn 47 (2002), Erg. 1, S. 124-126.
Schreiber, S.L. et al., "Atomic Structure of the Rapamycin Human Immunophilin FKBP-12 Complex," J. Am. Chem. Soc. 113:7433-7435 (1991).
Sen et al., "Topical heparin: A promising agent for the prevention of tracheal stenosis in airway surgery," J. Surg. Res (Epub ahead of print) Feb. 21, 2009.
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
SG201007602-4 Written Opinion dated Jun. 20, 2012.
SG201007602-4 Examination Report dated Feb. 13, 2013.
Shekunov et al. "Crystallization Processes in Pharmaceutical Technology and Drug Delivery Design." Journal of Crystal Growth 211 (2000), pp. 122-136.
Simpson et al., "Hyaluronan and hyaluronidase in genitourinary tumors." Front Biosci. 2009; 13:5664-5680.
Smith et al., "Mitomycin C and the endoscopic treatment of laryngotracheal stenosis: are two applications better than one?" Laryngoscope 119(2):272-283 (2009).
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008.
Szabadits et al., "Flexibility and trackability of laser cut coronary stent systems," Acta of Bioengineering and Biomechanics 11(3):11-18 (2009).
Testa, B. Prodrug research: futile or fertile? Biochem Pharmacol. Dec. 1, 2004;68(11):2097-106.
Thalmann et al., "Long-term experience with bacillus Calmette-Guerin therapy of upper urinary tract transitional cell carcinoma in patients not eligible for surgery," J Urol. 168(4 Pt 1):1381-1385 (2002).
U.S. Appl. No. 11/158,724 Office Action Mailed Sep. 17, 2009.
U.S. Appl. No. 11/158,724 Office Action Mailed Sep. 26, 2012.
U.S. Appl. No. 11/158,724 Office Action Mailed Sep. 8, 2008.
U.S. Appl. No. 11/877,591 Office Action Mailed Feb. 29, 2012.
U.S. Appl. No. 11/877,591 Office Action Mailed Sep. 21, 2012.
U.S. Appl. No. 11/995,685 Office Action Mailed Aug. 20, 2010.
U.S. Appl. No. 11/995,685 Office Action Mailed Nov. 24, 2009.
U.S. Appl. No. 11/995,687 Office Action Mailed Apr. 6, 2012.
U.S. Appl. No. 11/995,687 Office Action Mailed Sep. 28, 2011.
U.S. Appl. No. 12,298,459 Office Action Mailed Aug. 10, 2011.
U.S. Appl. No. 12/298,459 Office Action Mailed Apr. 6, 2012.
U.S. Appl. No. 12/426,198 Office Action Mailed Feb. 6, 2012.
U.S. Appl. No. 12/426,198 Office Action Mailed Mar. 23, 2011.
U.S. Appl. No. 12/443,959 Office Action Mailed Dec. 13, 2012.
U.S. Appl. No. 12/443,959 Office Action mailed Feb. 15, 2012.
U.S. Appl. No. 12/504,597 Final Office Action Mailed Oct. 3, 2012.
U.S. Appl. No. 12/504,597 Office Action Mailed Dec. 5, 2011.
U.S. Appl. No. 12/522,379 Office Action Mailed Dec. 26, 2012.
U.S. Appl. No. 12/595,848 Office Action Mailed Jan. 13, 2012.
U.S. Appl. No. 12/601,101 Office Action Mailed Dec. 27, 2012.
U.S. Appl. No. 12/601,101 Office Action Mailed Mar. 27, 2012.
U.S. Appl. No. 12/648,106 Final Office Action Mailed Sep. 25, 2012.
U.S. Appl. No. 12/648,106 Office Action Mailed Jan. 30, 2012.
U.S. Appl. No. 12/729,156 Final Office Action Mailed Oct. 16, 2012.
U.S. Appl. No. 12/729,156 Office Action Mailed Feb. 1, 2012.
U.S. Appl. No. 12/729,580 Office Action Mailed Apr. 10, 2012.
U.S. Appl. No. 12/729,580 Office Action Mailed Jan. 22, 2013.
U.S. Appl. No. 12/729,603 Final Office Action Mailed Oct. 10, 2012.
U.S. Appl. No. 12/729,603 Office Action Mailed Mar. 27, 2012.
U.S. Appl. No. 12/751,902 Office Action Mailed Jul. 13, 2012.
U.S. Appl. No. 12/595,848 Office Action Mailed Mar. 15, 2013.
U.S. Appl. No. 12/738,411 Final Office action Mailed Apr. 11, 2013.
U.S. Appl. No. 13/605,904 Office Action Mailed Nov. 27, 2012.
U.S. Appl. No. 12/762,007 Office action Mailed Feb. 11, 2013.
U.S. Appl. No. 13/384,216 Office action Mailed Apr. 24, 2013.
U.S. Appl. No. 13/340,472 Office action Mailed Apr. 26, 2013.
U.S. Appl. No. 12/729,156 Office action Mailed May 8, 2013.
U.S. Appl. No. 13/014,632 Office action Mailed May 8, 2013.
U.S. Appl. No. 13/086,335 Office action Mailed May 22, 2013.
U.S. Appl. No. 11/158,724 Office action Mailed May 23, 2013.
U.S. Appl. No. 12/601,101 Office action Mailed May 22, 2013.
U.S. Appl. No. 12,298,459 Office Action Mailed May 31, 2013.
U.S. Appl. No. 13/229,473 Office Action Mailed Jun. 17, 2013.
U.S. Appl. No. 13/605,904 Office Action Mailed Jun. 28, 2013.
U.S. Appl. No. 11/877,591 Office Action Mailed Jul. 1, 2013.
U.S. Appl. No. 12/748,134 Office Action Mailed Jul. 18, 2013.
U.S. Appl. No. 12/738,411 Office action Mailed Aug. 21, 2013.
U.S. Appl. No. 12/522,379 Final Office Action Mailed Aug. 28, 2013.
U.S. Appl. No. 12/648,106 Office Action Mailed Sep. 18, 2013.
Unger et al., "Poly(ethylene carbonate): A thermoelastic and biodegradable biomaterial for drug eluting stent coatings?" Journal fo Controlled Release, vol. 117, Issue 3, 312-321 (2007).
Verma et al., "Effect of surface properties on nanoparticle-cell interactions," Small 2010, 6, No. 1, 12-21.
Wagenlehner et al., "A pollen extract (Cernilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al. Controlled release of sirolimus from a multilayered PLGA stent matrix. Biomaterials 2000; 27:5588-95.
Wang et al., "Treatment with melagatran alone or in combination with thrombolytic therapy reduced ischemic brain injury," Exp. Neurol 213(1):171-175 (2008).

(56) References Cited

OTHER PUBLICATIONS

Warner et al., "Mitomycin C and airway surgery: how well does it work?" Ontolaryngol Head Neck Surg. 138(6):700-709 (2008).
Wermuth, CG Similarity in drugs: reflections on analogue design. Drug Discov Today. Apr. 2006;11(7-8):348-54.
Witjes et al., "Intravesical pharmacotherapy for non-muscle-invasive bladder cancer: a critical analysis of currently available drugs, treatment schedules, and long-term results," Eur. Urol. 2008; 53(1):45-52.
Wu et al., "Study on the preparation and characterization of biodegradable polylactide/multi-walled carbon nanotubes nanocomposites." Polymer 48 (2007) 4449-4458.
Xu et al., "Biodegradation of poly(1-lactide-co-glycolide tube stents in bile" *Polymer Degradation and Stability*. 93:811-817 (2008).
Xue et al., "Spray-as-you-go airway topical anesthesia in patients with a difficult airway: a randomized, double-blind comparison of 2% and 4% lidocaine," Anesth. Analg. 108(2): 536-543 (2009).
Yepes et al., "Tissue-type plasminogen activator in the ischemic brain: more than a thrombolytic," Trends Neurosci. 32(1):48-55 (2009).
Yousof et al., "Reveratrol exerts its neuroprotective effect by modulating mitochondrial dysfunction and associated cell death during cerebral ischemia," Brain Res. 1250:242-253 (2009).
Zhou et al. Synthesis and Characterization of Biodegradable Low Molecular Weight Aliphatic Polyesters and Their Use in Protein-Delivery Systems. J Appl Polym Sci 2004; 91:1848-56.
PCT/US2011/29667 International Search Report and Written Opinion mailed Jun. 1, 2011.
PCT/US2011/032371 International Search Report mailed Jul. 7, 2011.
PCT/US10/42355 Search Report mailed Sep. 2, 2010.
PCT/US10/28253 Search Report and Written Opinion mailed Dec. 6, 2010.
PCT/US10/28265 Search Report and Written Opinion mailed Dec. 3, 2010.
PCT/US10/28195 Search Report and Written Opinion mailed Jan. 21, 2011.
PCT/US10/31470 Search Report and Written Opinion mailed Jan. 28, 2011.
PCT/US10/29494 Search Report and Written Opinion mailed Feb. 7, 2011.
PCT/US11/22623 Search Report and Written Opinion mailed Mar. 28, 2011.
PCT/US2011/044263 International Search Report, International Preliminary Report on Patentability and Written Opinion dated Feb. 9, 2012.
PCT/US2007/82775 International Preliminary Report on Patentability dated Apr. 28, 2009.
PCT/US09/69603 International Search Report mailed Nov. 5, 2010.
PCT/US09/50883 International Preliminary Report on Patentability dated Jan. 18, 2011.
PCT/US10/28253 International Preliminary Report on Patentability dated Sep. 27, 2011.
PCT/US12/33367 International Search Report mailed Aug. 1, 2012.
PCT/US10/28195 International Preliminary Report on Patentability dated Oct. 6, 2011.
PCT/US2011/051092 International Preliminary Report on Patentability dated Mar. 21, 2013.
PCT/US10/42355 International Preliminary Report on Patentability dated Jan. 17, 2012.
PCT/US2011/67921 Search Report and Written Opinion mailed Jun. 22, 2012.
PCT/US2011/67921 International Preliminary Report on Patentability dated Jul. 11, 2013.

* cited by examiner

SYSTEM AND METHOD FOR ENHANCED ELECTROSTATIC DEPOSITION AND SURFACE COATINGS

FIELD OF THE INVENTION

The present invention relates generally to surface coatings and processes for making. More particularly, the invention relates to a system and method for enhancing charge of coating particles produced by rapid expansion of near-critical and supercritical solutions that improves quality of surface coatings.

BACKGROUND OF THE INVENTION

A high coating density is desirable for production of continuous thin films on surfaces of finished devices following post-deposition processing steps. Nanoparticle generation and electrostatic collection (deposition) processes that produce surface coatings can suffer from poor collection efficiencies and poor coating densities that result from inefficient packing of nanoparticles. Low-density coatings are attributed to the dendritic nature of the coating. "Dendricity" as the term is used herein is a qualitative measure of the extent of particle accumulations or fibers found on, the coating. For example, a high dendricity means the coating exhibits a fuzzy or shaggy appearance upon inspection due to fibers and particle accumulations that extend from the coating surface; the coating also has a low coating density. A low dendricity means the coating is smooth and uniform upon inspection and has a high coating density. New processes are needed that can provide coatings with a low degree of dendricity, suitable for use, e.g., on medical devices and other substrates.

SUMMARY OF THE INVENTION

Provided herein is a system for electrostatic deposition of particles upon a charged substrate to form a coating on a surface of the substrate, the system comprising: an expansion nozzle that releases coating particles having a first average electric potential suspended in a gaseous phase from a near-critical or supercritical fluid that is expanded through said nozzle; and an auxiliary emitter that generates a stream of charged ions having a second average potential in an inert carrier gas; whereby said coating particles interact with the charged ions and the carrier gas to enhance a charge differential between the coating particles and the substrate.

Provided herein is a system for electrostatic deposition of particles upon a charged substrate to form a coating on a surface of the substrate, the system comprising: an expansion nozzle that releases coating particles having a first average electric potential suspended in a gaseous phase from a near-critical or supercritical fluid that is expanded through the nozzle; and an auxiliary emitter that generates a stream of charged ions having a second average electric potential in an inert carrier gas; whereby the coating particles interact with the charged ions and the carrier gas to enhance a potential differential between the coating particles and the substrate.

In some embodiments, the coating particles have a first velocity upon release of the coating particles from the expansion nozzle that is less than a second velocity of the coating particles when the coating particles impact the substrate. In some embodiments, attraction of the coating particles to the substrate is increased as compared to attraction of the coating particles to the substrate in a system without the auxiliary emitter.

In some embodiments, the first average electric potential is different than the second average electric potential. In some embodiments, an absolute value of the first average electric potential is less than an absolute value of the second average electric potential, and wherein a polarity the charged ions is the same as a polarity of the coating particles.

In some embodiments, the auxiliary emitter comprises an electrode having a tapered end that extends into a gas channel that conducts the stream of charged ions in the inert carrier gas toward the charged coating particles. In some embodiments, the auxiliary emitter further comprises a capture electrode. In some embodiments, the auxiliary emitter comprises a metal rod with a tapered tip and a delivery orifice.

In some embodiments, the substrate is positioned in a circumvolving orientation around the expansion nozzle.

In some embodiments, the substrate comprises a conductive material. In some embodiments, the substrate comprises a semi-conductive material. In some embodiments, the substrate comprises a polymeric material.

In some embodiments, the charged ions at the second electric potential are a positive corona or a negative corona positioned between the expansion nozzle and the substrate. In some embodiments, the charged ions at the second electric potential are a positive corona or a negative corona positioned between the auxiliary emitter and the substrate.

In some embodiments, the coating particles comprises at least one of: polylactic acid (PLA); poly(lactic-co-glycolic acid) (PLGA); polycaprolactone (poly(e-caprolactone)) (PCL), polyglycolide (PG) or (PGA), poly-3-hydroxybutyrate; LPLA poly(l-lactide), DLPLA poly(dl-lactide), PDO poly(dioxolane), PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid) and blends, combinations, homopolymers, condensation polymers, alternating, block, dendritic, crosslinked, and copolymers thereof.

In some embodiments, the coating particles comprise at least one of: polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene-C, polyethylene-co-vinyl acetate, polyalkyl methacrylates, polyalkylene-co-vinyl acetate, polyalkylene, polyalkyl siloxanes, polyhydroxyalkenoate, polyfluoroalkoxyphasphazine, poly(styrene-b-isobutylene-b-styrene), poly-butyl methacrylate, poly-byta-diene, and blends, combinations, homopolymers, condensation polymers, alternating, block, dendritic, crosslinked, and copolymers thereof.

In some embodiments, the coating particles have a size between about 0.01 micrometers and about 10 micrometers.

In some embodiments, the second velocity is in the range from about 0.1 cm/sec to about 100 cm/sec. In some embodiments, the coating has a density on the surface in the range from about 1 volume % to about 60 volume %.

In some embodiments, the coating is a multilayer coating. In some embodiments, the substrate is a medical implant. In some embodiments, the substrate is an interventional device. In some embodiments, the substrate is a diagnostic device. In some embodiments, the substrate is a surgical tool. In some embodiments, the substrate is a stent.

In some embodiments, the coating is non-dendritic as compared to a baseline average coating thickness. In some embodiments, no coating extends more than 0.5 microns from the baseline average coating thickness. In some embodiments, no coating extends more than 1 micron from the baseline average coating thickness.

In some embodiments, the coating is non-dendritic such that there is no surface irregularity of the coating greater than 0.5 microns. In some embodiments, the coating is non-dendritic such that there is no surface irregularity of the coating greater than 1 micron. In some embodiments, the coating is non-dendritic such that there is no surface irregularity of the coating greater than 2 microns following sintering of the coated substrate. In some embodiments, the coating is non-dendritic such that there is no surface irregularity of the coating greater than 3 microns following sintering of the coated substrate.

Provided herein is a system for enhancing charge of solid coating particles produced from expansion of a near-critical or supercritical solution for electrostatic deposition upon a charged substrate as a coating. The system is characterized by: an expansion nozzle that releases charged coating particles having a first potential suspended in a gaseous phase from a near-critical or supercritical fluid that is expanded through the expansion nozzle; and an auxiliary emitter that generates a stream of selectively charged ions having a second potential in an inert carrier gas stream. Charged coating particles interact with charged ions in the gas stream to enhance a charge differential between the charged coating particles and the substrate. The substrate is positioned within an electric field and is subject to that field, which increases the velocity at which the charged coating particles impact the substrate. The auxiliary emitter includes a metal rod electrode having a tapered end that extends into a gas channel containing a flowing inert carrier gas. The auxiliary emitter further includes a counter-electrode that operates at a potential relative to the rod electrode. The counter-electrode may be in the form of a ring, with all points on the ring being equidistant from the tapered tip. The counter electrode can be grounded or oppositely charged. A corona is generated at the pointed tip of the tapered rod, emitting a stream of charged ions. The gas channel conducts the charged ions in the inert carrier gas into the deposition enclosure, where they interact with the coating particles produced by the fluid expansion process. The substrate to be coated by the coating particles may be positioned in a circumvolving orientation around the expansion nozzle. In one embodiment, the substrate is positioned on a revolving stage or platform that provides the circumvolving orientation around the expansion nozzle. Substrates can be individually rotated clockwise or counterclockwise through a rotation of 360 degrees. The substrate can include a conductive material, a metallic material, and/or a semi-conductive material. The coating that results on the substrate has: an enhanced surface coverage, an enhanced surface coating density, and minimized dendrite formation.

Provided herein is a method for forming a coating on a surface of a substrate, comprising: establishing an electric field between the substrate and a counter electrode; producing coating particles suspended in a gaseous phase of an expanded near-critical or supercritical fluid having an first average electric potential; and contacting the coating particles with a stream of charged ions at a second average potential in an inert carrier gas to increase the charge differential between the coating particles and the substrate.

Provided herein is a method for coating a surface of a substrate with a preselected material forming a coating, comprising the steps of: establishing an electric field between the substrate and a counter electrode; producing coating particles suspended in a gaseous phase of an expanded near-critical or supercritical fluid having an first average electric potential; and contacting the coating particles with a stream of charged ions at a second average potential in an inert carrier gas to increase the potential differential between the coating particles and the substrate.

In some embodiments, the coating particles have a first velocity upon release of the coating particles from the expansion nozzle that is less than a second velocity of the coating particles when the coating particles impact the substrate. In some embodiments, attraction of the coating particles to the substrate is increased as compared to attraction of the coating particles to the substrate in a system without the auxiliary emitter. In some embodiments, the first average electric potential is different than the second average electric potential. In some embodiments, an absolute value of the first average electric potential is less than an absolute value of the second average electric potential, and wherein a polarity the charged ions is the same as a polarity of the coating particles.

In some embodiments, the second velocity is in the range from about 0.1 cm/sec to about 100 cm/sec.

In some embodiments, the coating particles have a size between about 0.01 micrometers and about 10 micrometers.

In some embodiments, the substrate has a negative polarity and an enhanced charge of the coating particles following the contacting step is a positive charge; or wherein the substrate has a positive polarity and an enhanced charge of the coating particles following the contacting step is a negative charge.

In some embodiments, the contacting step comprises forming a positive corona or forming a negative corona positioned between the expansion nozzle and the substrate. In some embodiments, the contacting step comprises forming a positive corona or forming a negative corona positioned between the auxiliary emitter and the substrate.

In some embodiments, the coating has a density on the surface from about 1 volume % to about 60 volume %.

In some embodiments, the coating particles comprise at least one of: a polymer, a drug, a biosorbable material, a protein, a peptide, and a combination thereof.

In some embodiments, the coating particles comprises at least one of: polylactic acid (PLA); poly(lactic-co-glycolic acid) (PLGA); polycaprolactone (poly(e-caprolactone)) (PCL), polyglycolide (PG) or (PGA), poly-3-hydroxybutyrate; LPLA poly(l-lactide), DLPLA poly(dl-lactide), PDO poly(dioxolane), PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid) and blends, combinations, homopolymers, condensation polymers, alternating, block, dendritic, crosslinked, and copolymers thereof. In some embodiments, the coating on the substrate comprises polylactoglycolic acid (PLGA) at a density greater than 5 volume %.

In some embodiments, the coating particles comprise at least one of: polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene-C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly (styrene-b-isobutylene-b-styrene), poly-butyl methacrylate, poly-byta-diene, and blends, combinations, homopolymers, condensation polymers, alternating, block, dendritic, crosslinked, and copolymers thereof.

In some embodiments, the coating particles include a drug comprising one or more of: rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allylrapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 40-O-(6-Hydroxy)hexyl-rapamycin 40-O-[2-(2-Hydroxy)ethoxy]ethyl-rapamycin 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1,2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, isomers, racemates, diastereoisomers, prodrugs, hydrate, ester, or analogs thereof.

In some embodiments, the second velocity is in the range from about 0.1 cm/sec to about 100 cm/sec.

In some embodiments, the method further includes the step of sintering the coating at a temperature in the range from about 25° C. to about 150° C. to form a dense, thermally stable film on the surface of the substrate.

In some embodiments, the method further includes the step of sintering the coating in the presence of a solvent gas to form the dense, thermally stable film on the surface of the substrate.

In some embodiments, the producing and the contacting steps, at least, are repeated to form a multilayer film.

In some embodiments, the substrate is at least a portion of a medical implant. In some embodiments, the substrate is an interventional device. In some embodiments, the substrate is a diagnostic device. In some embodiments, the substrate is a surgical tool. In some embodiments, the substrate is a stent. In some embodiments, the substrate is a medical balloon.

In some embodiments, the coating is non-dendritic as compared to a baseline average coating thickness. In some embodiments, no coating extends more than 0.5 microns from the baseline average coating thickness. In some embodiments, no coating extends more than 1 micron from the baseline average coating thickness.

In some embodiments, the coating is non-dendritic such that there is no surface irregularity of the coating greater than 0.5 microns. In some embodiments, the coating is non-dendritic such that there is no surface irregularity of the coating greater than 1 micron. In some embodiments, the coating is non-dendritic such that there is no surface irregularity of the coating greater than 2 microns following sintering of the coated substrate. In some embodiments, the coating is non-dendritic such that there is no surface irregularity of the coating greater than 3 microns following sintering of the coated substrate.

Provided herein is a method for coating a surface of a substrate with a preselected material, forming a coating. The method includes the steps of: establishing an electric field between the substrate and a counter electrode; producing solid solute (coating) particles from a near-critical or supercritical expansion process at an average first electric potential that are suspended in a gaseous phase of the expanded near-critical or supercritical fluid; and contacting the solid solute (coating) particles with a stream of charged ions at a second potential in an inert carrier gas to increase the charge differential between the particles and the substrate, thereby increasing the velocity at which the solute particles impact upon the substrate. The charge differential increases the attraction of the charged particles for the substrate. The solid solute particles are thus accelerated through the electric field, which increases the velocity at which the solute particles impact the surface of the substrate. High impact velocity and enhanced coating efficiency of the coating particles produce a coating on the substrate with an optimized microstructure and a low surface dendricity. The charged coating particles have a size that may be between about 0.01 micrometers and 10 micrometers. In one embodiment, the substrate includes a negative polarity and the enhanced charge of the solid solute particles is a positive enhanced charge. In another embodiment, the substrate includes a positive polarity and the enhanced charge of the solid solute particles is a negative enhanced charge. The increase in charge differential increases the velocity of the solid solute particles through an electric field that increases the force of impact of the particles against the surface of the substrate. The method further includes the step of sintering the coating that is formed during the deposition/collection process to form a thermally stable continuous film on the substrate, e.g., as detailed in U.S. Pat. No. 6,749,902, incorporated herein in its entirety. Various sintering temperatures and/or exposure to a gaseous solvent can be used. In some embodiments, sintering temperatures for forming dense, thermally stabile from the collected coating particles are selected in the range from about 25° C. to about 150° C. In one embodiment described hereafter, the invention is used to deposit biodegradable polymer and/or other coatings to surfaces that are used to produce continuous layers or films, e.g., on biomedical and/or drug-eluting devices (e.g., medical stents), and/or portions of medical devices. The coatings can also be applied to other medical devices and components including, e.g., medical implant devices such as, e.g., stents, medical balloons, and other biomedical devices.

Provided herein is a coating on a surface of a substrate produced by any of the methods described herein. Provided herein is a coating on a surface of a substrate produced by any of the systems described herein.

The final film from the coating can be a single layer film or a multilayer film. For example, the process steps can be repeated one or more times and with various materials to form a multilayer film on the surface of the substrate. In one embodiment, the medical device is a stent. In another embodiment, the substrate is a conductive metal stent. In yet another embodiment, the substrate is a non-conductive polymer medical balloon. The coating particles include materials that consist of: polymers, drugs, biosorbable materials, proteins, peptides, and combinations of these materials. In various embodiments, impact velocities at which the charged coating particles impact the substrate are from about 0.1 cm/sec to about 100 cm/sec. In some embodiments, the polymer that forms the solute particles is a biosorbable organic polymer and the supercritical fluid solvent includes a fluoropropane. In one embodiment, the coating is a polylactoglycolic acid (PLGA) coating that includes a coating density greater than (>) about 5 volume %.

In one embodiment, the charged ions, at the selected potential are a positive corona positioned between an emission location and a deposition location of the substrate. In another embodiment, the charged ions at the selected potential are a negative corona positioned between an emission location and a deposition location of the substrate.

While the invention is described herein with reference to high-density coatings deposited onto medical device surfaces, in particular, stent surfaces, the invention is not limited thereto. All substrates as will be envisioned by those of ordinary skill in the art in view of the disclosure are within the scope of the invention. No limitations are intended.

DETAILED DESCRIPTION

Figure 1:
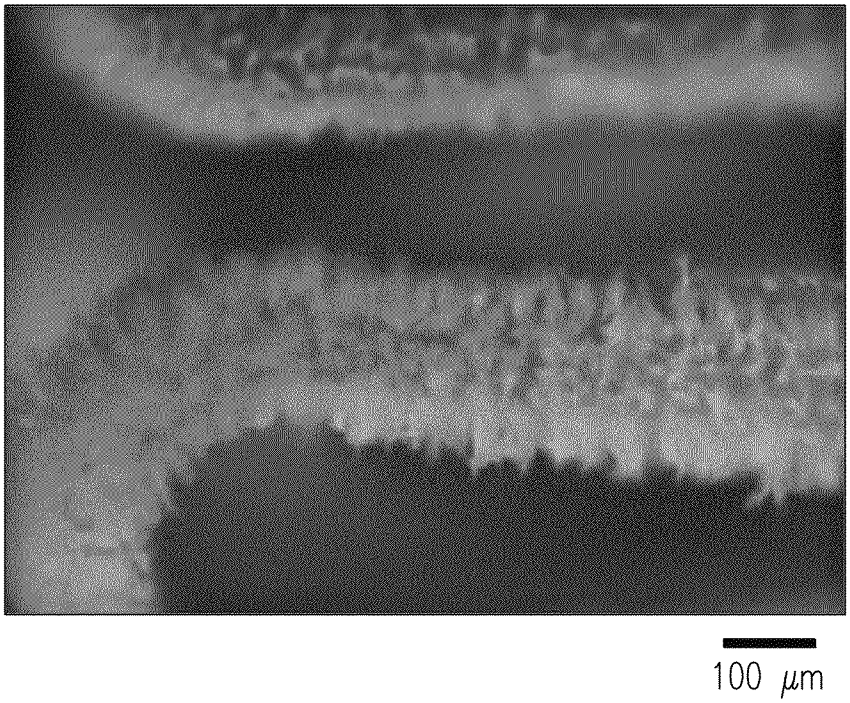
FIG. 1 is an optical micrograph showing an embodiment dendritic coating produced by the e-RESS process that does not include the auxiliary emitter and charged ions described herein.

The invention is a system and method for enhancing electrostatic deposition of charged particles upon a charged substrate forming nanoparticle coatings. The invention improves collection efficiency, microstructure, and density of coatings, which minimizes dendricity of the coating on the selected substrate. Solid solute (coating) particles are generated from near-critical and supercritical solutions by a process of Rapid Expansion of (near-critical or) Supercritical Solutions, known as the RESS process.

The term "e-RESS" refers to the process for forming coatings by electrostatically collecting RESS expansion particles.

The term "near-critical fluid" as used herein means a fluid that is a gas at standard temperature and pressure (i.e., STP) and presently is at a pressure and temperature below the critical point, and where the fluid density exceeds the critical density ($\rho_c$).

The term "supercritical fluid" means a fluid at a temperature and pressure above its critical point. The invention finds application in the generation and efficient collection of these particles producing coatings with a low dendricity, e.g., for deposition on medical stents and other devices.

Various aspects of the RESS process are detailed in U.S. Pat. Nos. 4,582,731; 4,734,227; 4,734,451; 6,749,902; and 6,756,084 assigned to Battelle Memorial Institute, which patents are incorporated herein in their entirety.

Solid solute particles produced by the invention are governed by various electrostatic effects, the fundamentals of which are detailed, e.g., in "Aerosol Technology: Properties, Behavior, and Measurement of Airborne Particles" (William C. Hinds, Author, John Wiley & Sons, Inc., New York, N.Y., Ch. 15, Electrical Properties, pp. 284-314, 1982).

Embodiments of the invention comprise an auxiliary emitter and/or a process of using the same that enhances charge of RESS-generated coating particles, which improves the collection efficiency and deposition. The auxiliary emitter delivers a corona that enhances the charge of the solid solute particles. The term "corona" as used herein means an emission of charged ions accompanied by ionization of the surrounding atmosphere. Both positive and negative coronas may be used with the invention, as detailed further herein. Fundamentals of electrostatic processes including formation of coronal discharges are detailed, e.g., in the "Encyclopedia of Electrical and Electronics Engineering" (John Wiley & Sons, Inc., John G. Webster (Editor), Volume 7, Electrostatic Processes, 1999, pp. 15-39), which reference is incorporated herein. The enhanced charge further increases the velocity of impact of the coating particles on a selected substrate, improving the collection efficiency on the coating surface. The term "coating" as used herein refers to one or more layers of electrostatically-deposited coating particles on a substrate or surface.

Embodiments of the invention enhance the charge and collection efficiency of the coating particles that improves the microstructure, weight, and/or the coating density, which minimizes formation of dendrites during the deposition process. Thus, the quality of the particle coating on the substrate is enhanced. When sintered, the coating particles subsequently coalesce to form a continuous, uniform, and thermally stable film.

The invention thus produces high-density coatings that when deposited on various substrate surfaces are amenable to sintering into high quality films. The term "high density" as used herein means an electrostatic near-critical or supercritical solution-expanded (RESS) coating on a substrate having a coating density of from about 1 volume % to about 60 volume %, and the coating has a low-surface dendricity rating at or below 1 as measured, e.g., from a cross-sectional view of the coating and the substrate by scanning-electron micrograph (SEM). The term "volume %" is defined herein as the ratio of the volume of solids divided by the total volume times 100.

Another definition of a coating that is "high density" as described herein (or systems comprising such coatings, or processes producing such coating) includes a test for packing density of the coating in which the coating is determined to be non-dendritic as compared to a baseline average coating thickness for substrates coated at the same settings. That is, for a particular coating process set of settings for a given substrate (before sintering), a baseline average coating thickness is determined by determining and averaging coating thickness measurements at multiple locations (e.g. 3 or more, 5 or more, 9 or more, 10 or more) and for several substrates (if possible). The baseline average coating thickness and/or measurement of any coated substrate prior to sintering may be done, for example, by SEM or another visualization method having the ability to measure and visualize to the coating with accuracy, confidence and/or reliability.

Once the average is determined, for coatings on substrates coated at such settings can be compared to the average coating thickness for these settings. Multiple locations of the substrate may be tested to ensure the appropriate confidence and/or reliability. In some embodiments, a "non-dendritic" coating has no coating that extends more than 1 micron from the average coating thickness. In some embodiments, a "non-dendritic" coating has no coating that extends more than 0.5 microns from the average coating thickness. In some embodiments, a "non-dendritic" coating has no coating that extends more than 1.5 microns from the average coating thickness. In some embodiments, a "non-dendritic" coating has no coating that extends more than 2 microns from the average coating thickness. In some embodiments, a "dendritic" coating has coating that extends more than 0.5 microns from the average coating thickness. In some embodiments, a "dendritic" coating has coating that extends more than 1 micron from the average coating thickness. In some embodiments, a "dendritic" coating has coating that extends more than 1.5 microns from the average coating thickness. In some embodiments, a "dendritic" coating has coating that extends more than 2 microns from the average coating thickness.

In some embodiments, the number of sample locations on the coated substrate is chosen to ensure 90% confidence and 90% reliability that the coating is non-dendritic. In some embodiments, the number of sample locations on the coated substrate is chosen to ensure 95% confidence and 90% reliability that the coating is non-dendritic. In some embodiments, the number of sample locations on the coated substrate is chosen to ensure 95% confidence and 95% reliability that the coating is non-dendritic. In some embodiments, the number of sample locations on the coated substrate is chosen to ensure 99% confidence and 95% reliability that the coating is non-dendritic. In some embodiments, the number of sample locations on the coated substrate is chosen to ensure 99% confidence and 99% reliability that the coating is non-dendritic.

In some embodiments, at least 9 sample locations are reviewed, three at about a first end, 3 at about the center of the substrate, and 3 at about a second end of a substrate, and if none of the locations exceed the specification (e.g., greater than 2 microns from the average, greater than 1.5 microns from the average, greater than 1 micron from the average, or greater than 0.5 microns from the average), then the coating is non-dendritic. In some embodiments, the entire substrate is reviewed and compared to the average coating thickness to ensure the coating is non-dendritic.

In some embodiments, each substrate is compared to its own average coating thickness, and not that of other substrates processed at the same or similar coating process settings.

In embodiments where multiple coating layers are created on a substrate, with a sintering step following each coating, this test may be performed following any particular coating step just prior to sintering. The variability in coating thickness of a previous sintered layer may (or may not) be accounted for in the calculations such that a second and/or subsequent layer may allow for greater variation from the average coating thickness and still be considered "non-dendritic."

In some embodiments, a coated substrate (before sintering) is non-dendritic if there is no surface irregularity greater than 0.5 microns. That is, a measurement from the base (or trough) of the coating to a peak of the coating does not exceed 0.5 microns. In some embodiments, a coated substrate (before sintering) is non-dendritic if there is no surface irregularity greater than 1 micron. That is, a measurement from the base (or trough) of the coating to a peak of the coating does not exceed 1 micron. In some embodiments, a coated substrate (before sintering) is non-dendritic if there is no surface irregularity greater than 1.5 microns. That is, a measurement from the base (or trough) of the coating to a peak of the coating does not exceed 1.5 microns. In some embodiments, a coated substrate (before sintering) is non-dendritic if there is no surface irregularity greater than 2 microns. That is, a measurement from the base (or trough) of the coating to a peak of the coating does not exceed 2 microns. The entire substrate does not require review and testing for these to be met, rather, as noted above, a sampling resulting in a particular confidence/reliability (for example, 90%/90%, 90%/95%, 95%/95%, 99%/95%, and/or 99%/99%) is sufficient.

In some embodiments, a coated substrate (post sintering) is non-dendritic if there is no surface irregularity greater than 2 microns. That is, a measurement from the base (or trough) of the coating to a peak of the coating does not exceed 2 microns if measured after sintering. In some embodiments, a coated substrate (post sintering) is non-dendritic if there is no surface irregularity greater than 2.5 microns. That is, a measurement from the base (or trough) of the coating to a peak of the coating does not exceed 2.5 microns if measured after sintering. In some embodiments, a coated substrate (post sintering) is non-dendritic if there is no surface irregularity greater than 3 microns. That is, a measurement from the base (or trough) of the coating to a peak of the coating does not exceed 3 microns if measured after sintering. The entire substrate does not require review and testing for these to be met, rather, as noted above, a sampling resulting in a particular confidence/reliability (for example, 90%/90%, 90%/95%, 95%/95%, 99%/95%, and/or 99%/99%) is sufficient. In embodiments where multiple coating layers are created on a substrate, with a sintering step following each coating, this confidence/reliability testing may be performed following any particular sintering step. No limitations are intended.

Figure 6:
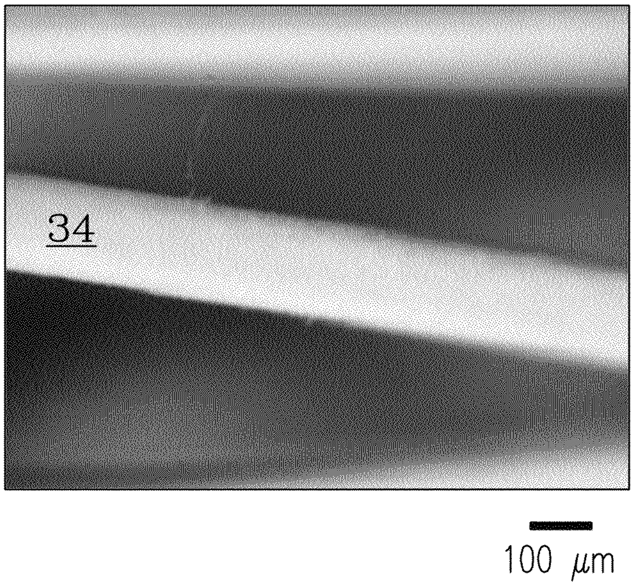
FIG. 6 is an optical micrograph showing an embodiment non-dendritic coating produced by an enhanced e-RESS coating process as described herein.

For example, FIG. 1 shows a coated substrate (100× magnification) with a dendritic coating (PLGA), where the average thickness of the coating is about 25 microns, and where the coating extends greater than 10 microns from this average. The dendritic coating also shows a surface irregularity, from a trough to a peak, greater than 25 microns. The dendritic coating was produced by a Rapid Expansion of Supercritical Solution (RESS) process that does not include use of the auxiliary emitter and charged ions described herein. FIG. 6 (described further herein) shows a coated substrate (160× magnification) with a non-dendritic coating, where the average thickness is about 10 microns, and where no coating extends greater than 1 micron from this average. The non-dendritic coating also shows no surface irregularity greater than 2 microns, from a trough to a peak. The non-dendritic coating was produced by an electrostatic Rapid Expansion of Supercritical Solution (e-RESS) process that includes use of an auxiliary emitter and charged ions described herein.

The term "sintering" used herein refers to processes—with or without the presence of a gas-phase solvent to reduce sintering temperature—whereby e-RESS particles initially deposited as a coating coalesce, forming a continuous dense, thermally stable film on a substrate. Coatings can be sintered by the process of heat-sintering at selected temperatures described herein or alternatively by gas-sintering in the presence of a solvent gas or supercritical fluid as detailed, e.g., in U.S. Pat. No. 6,749,902, which patent is incorporated herein in its entirety. The term "film" as used herein refers to a continuous layer produced on the surface after sintering of an e-RESS-generated coating.

Embodiments of the invention find application in producing coatings of devices including, e.g., medical stents that are coated, e.g., with time-release drugs for time-release drug applications. These and other enhancements and applications are described further herein. While the process of coating in accordance with the invention will be described in reference to the coating of medical stent devices, it should be strictly understood that the invention is not limited thereto. The person or ordinary skill in the art will recognize that the invention can be used to coat a variety of substrates for various applications. All coatings as will be produced by those of ordinary skill in view of the disclosure are within the scope of the invention. No limitations are intended.

Figure 2:
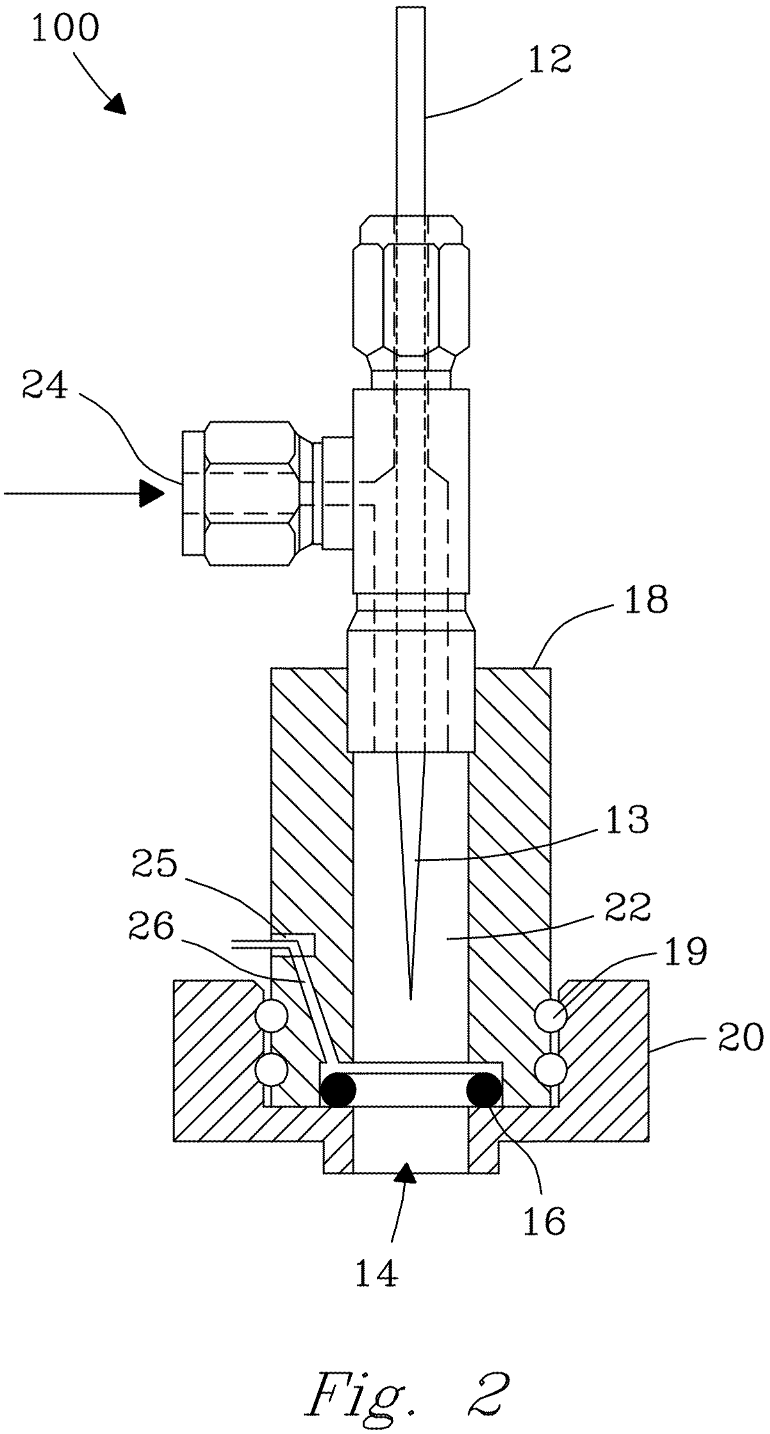
FIG. 2 is a schematic diagram of one embodiment of the invention.
Figure 4:
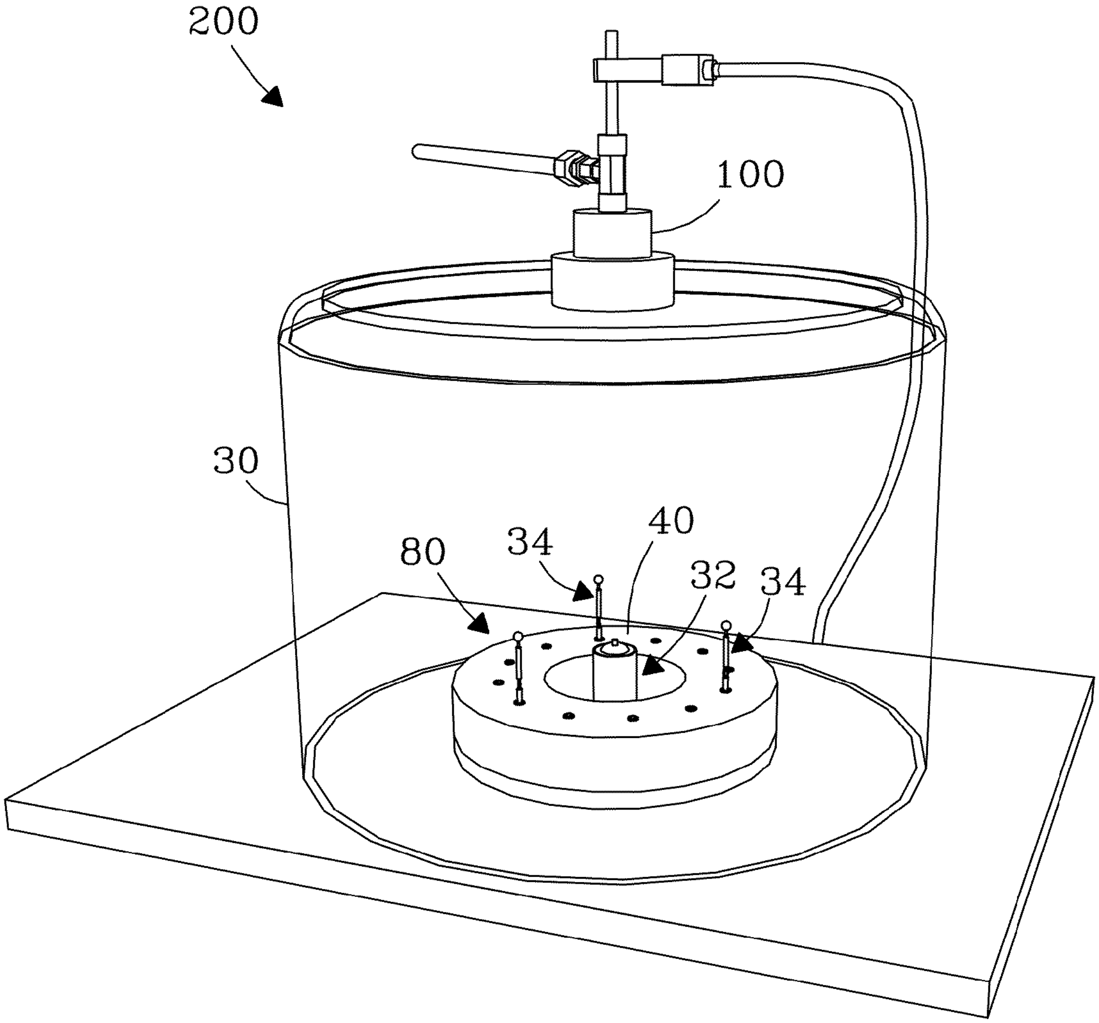
FIG. 4 shows an e-RESS system that includes an embodiment of the invention.

FIG. 2 is a schematic diagram of an auxiliary emitter 100, according to an embodiment of the invention. Auxiliary emitter 100 is a charging device that enhances the charge of solid solute (coating) particles formed by the e-RESS process. The enhanced charge transferred to the coating particles increases the impact velocity of the particles on the substrate surface. e-RESS-generated coating particles that form on the surface of the substrates when utilizing auxiliary emitter 100 have enhanced surface coverage, enhanced surface coating density, and lower dendricity than coatings produced without it. In the exemplary embodiment, auxiliary emitter 100 includes a metal rod 12 (e.g., ⅛-inch diameter), as a first auxiliary electrode 12, configured with a tapered or pointed tip 13. Tip 13 provides a site where charged ions (corona) are generated. The charged ions are subsequently delivered to the deposition vessel, described further herein in reference to FIG. 4. In the exemplary embodiment, rod 12 is grounded (i.e., has a zero potential), but is not limited thereto. For example, in an alternate implementation, emitter tip 13 of rod 12 has a high potential. No limitations are intended. Emitter 100 further includes a collector 16, or second auxiliary electrode 16, of a ring or circular counter-electrode design (e.g., ⅛-inch diameter, 0.75 I.D. copper) that is required for formation of the corona at the tapered tip 13, but the invention is not limited thereto. Emitter 100 further includes a gas channel 22 that receives a flow of inert carrier gas (e.g., dry nitrogen or another dry gas having a relative humidity of about 0 wherein "about" allows for variations of 1% maximum, 0.5% maximum, 0.25% maximum, 0.1% maximum, 0.01% maximum, and/or 0.001% maximum) delivered through gas inlet 24 at a preselected rate and pressure (e.g., 4.5 L/min @20 psi). Rate and pressures are not limited. Emitter tip 13 extends a preselected distance (e.g., 1 cm to 2 cm) into gas channel 22, which distance can be varied to establish a preselected current between rod 12 and collector 16. A flow of inert gas through channel 22 carries charged ions produced by the corona through orifice 14 into the deposition vessel (FIG. 4). In a typical run, a potential of about 5 kV (+ or −) is applied to collector 16, which establishes a current of 1 microamperes (μA) at the 1 cm distance from tip 13, but distance and potential are not limited thereto as will be understood by those of ordinary skill in the electrical arts. For example, distance and potentials are selected and applied such that high currents sufficient to maximize charge delivered to the deposition vessel are generated. In various embodiments, currents can be selected in the range from about 0.05 μA to about 10 μA. Thus, no limitations are intended.

In the instant embodiment, collector 16 is positioned within auxiliary body 18. Auxiliary body 18 inserts into, and couples snugly with, base portion 20, e.g., via two (2) O-rings 19 composed of, e.g., a fluoroelastomer (e.g., VITON®, DuPont, Wilmington, Del., USA), or another suitable material positioned between auxiliary body 18 and base portion 20. Base portion 20 is secured to the deposition vessel (FIG. 4) such that auxiliary body 18 can be detached from base portion 20. The detachability of auxiliary body 18 from base portion 20 allows for cleaning of auxiliary electrodes 12, 16. Auxiliary body 18 and base portion 20 are composed of, e.g., a high tensile-strength machinable polymer (e.g., polyoxymethylene also known as DELRIN®, DuPont, Wilmington, Del., USA) or another structurally stable, insulating material. Auxiliary body 18 and base 20 can be constructed as individual components or collectively as a single unit. No limitations are intended. Gas channel 22 is located within auxiliary body 18 to provide a flow of inert gas (e.g., dry nitrogen or another dry gas having a relative humidity of about 0 wherein "about" allows for variations of 1% maximum, 0.5% maximum, 0.25% maximum, 0.1% maximum, 0.01% maximum, and/or 0.001% maximum) that sweeps charged ions generated in emitter 100 into the deposition vessel (FIG. 4) and further minimizes coating particles from coating emitter tip 13 during the coating run. Auxiliary body 18 further includes a conductor element 26 positioned within a conductor channel 25 that provides coupling between collector 16 and a suitable power supply (not shown). Configuration of power coupling components is exemplary and is not intended to be limiting. For example, other electrically-conducting and/or electrode components as will be understood by those of ordinary skill in the electrical arts can be coupled without limitation.

Figure 3A:
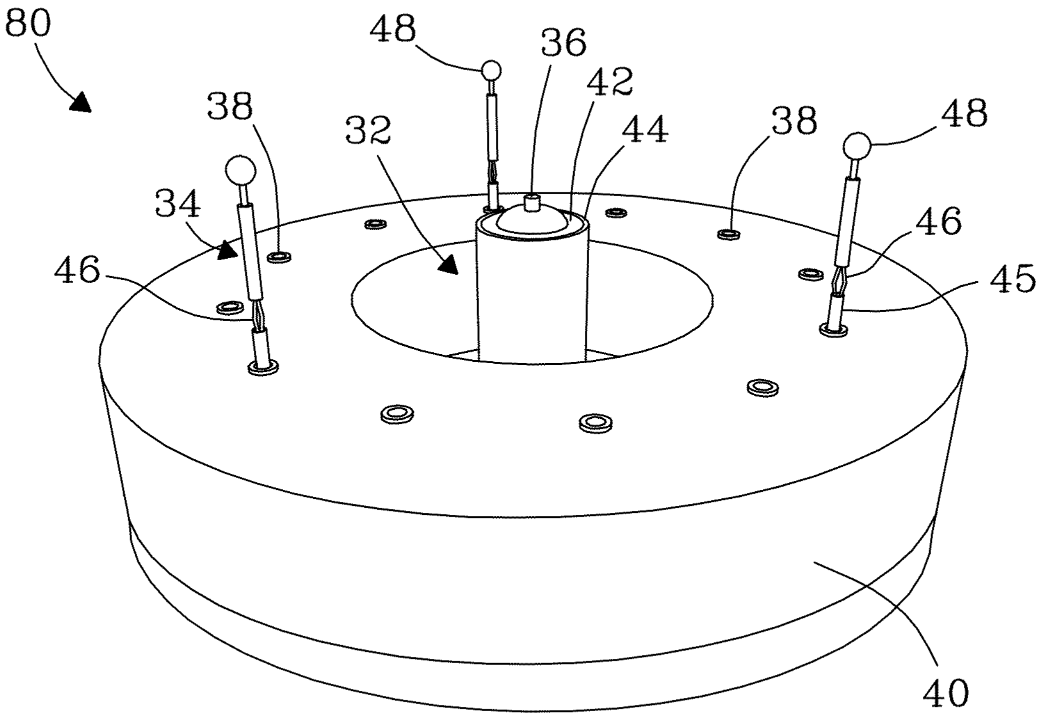
FIG. 3 is a top perspective view of a base platform that includes a RESS expansion nozzle, according to an embodiment of the invention.
Figure 3B:
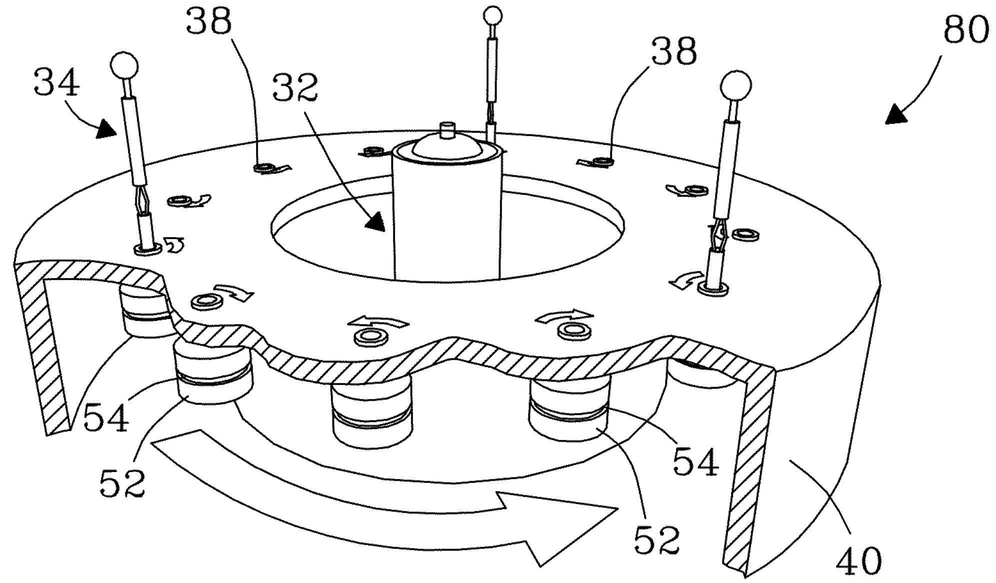

FIG. 3 is a top perspective view of a RESS base portion 80 (base), according to an embodiment of the invention. RESS base portion 80 includes an expansion nozzle assembly 32, equipped with a spray nozzle orifice 36. In standard mode, nozzle orifice 36 releases a plume of expanding supercritical or near-critical solution containing at least one solute (e.g., a polymer, drug, or other combinations of materials) dissolved within the supercritical or near-critical solution. During the RESS process, the solution expands through nozzle assembly 32 forming solid solute particles of a suitable size that are released through nozzle orifice 36. While release is described, e.g., in an upward direction, direction of release of the plume is not limited. Nozzle orifice 36 can also deliver a plume of charged coating particles absent the expansion solvent, e.g., as an electrostatic dry powder, which process is detailed in patent publication number WO 2007/011707 A2 (assigned to MiCell Technologies, Inc., Raleigh, N.C., USA), which reference is incorporated herein in its entirety. In the instant embodiment, nozzle assembly 32 includes a metal sheath 44 as a first e-RESS electrode 44 (central post electrode 44) that surrounds an insulator 42 material (e.g., DELRIN®) to separate metal sheath 44 from nozzle orifice 36. First e-RESS electrode 44 may be grounded so as to have no detectable current, but is not limited thereto as described herein. Expansion nozzle assembly 32 is mounted at the center of a rotating stage 40 and positioned equidistant from the metal stents (substrates) 34 mounted to stage 40, but position in the exemplary device is not intended to be limiting. Stents 34 serve collectively as a second e-RESS electrode 34. A metal support ring (not shown) underneath stage 40 extends around the circumference of stage 40 and couples to the output of a high voltage, low current DC power supply (not shown) via a cable (not shown) fed through stage 40. The end of the cable is connected to the metal support ring and to stage mounts 38 into which stents 34 are mounted on stage 40. The power supply provides power for charging of substrates 34 (stents 34). Stents 34 are mounted about the circumference along an arbitrary line of stage 40, but mounting position is not limited. Stents 34 are suspended above stage 40 on wire holders 46 (e.g., 316-Stainless steel) that run through the center of each stent 34. Stents 34 positioned on wire holders 46 are supported on holder posts 45 that insert into individual stage mounts 38 on stage 40. A plastic bead (disrupter) 48 is placed at the top end of each wire holder 46 to prevent coronal discharge and to maintain a proper electric field and for proper formation of the coating on each stent 34. Mounts 38 rotate through 360 degrees, providing rotation of individual stents 34. Stage 40 also rotates through 360 degrees. Two small DC-electric motors (not shown) installed underneath stage 40 provide rotation of individual substrates 34 (stents 34) and rotation of stage 40, respectively. Rate at which stents 34 are rotated may be about 10 revolutions per minute to provide for uniform coating during the coating process, but rate and manner of revolution is not limited thereto. Stage 40 also rotates in some embodiments at a rate of about 10 revolutions per minute during the coating process, but rate and manner of revolution are again not limited thereto. Rotation of mounts 38 and stage 40 at preselected rates can be performed by various methods as will be understood by those of ordinary skill in the mechanical arts. No limitations are intended. Rotation of both stage 40 and stents 34 provides uniform and maximum exposure of each stent 34 or substrate surface to the coating particles delivered from RESS nozzle assembly 32. Location of expansion nozzle assembly 32 is not limited, and is selected such that a suitable electric field is established between nozzle assembly 32 and stents 34. Thus, configuration is not intended to be limited. A typical operating voltage applied to stents 34 is −15 kV. Stage 40 is fabricated from an engineered thermoplastic or insulating polymer having excellent strength, stiffness, and dimensional stability, including, e.g., polyoxymethylene (also known by the trade name DELRIN®, DuPont, Wilmington, Del., USA), or another suitable material, e.g., as used for the manufacture of precision parts, which materials are not intended to be limited.

System for Deposition of e-RESS-Generated Particles for Coating Surfaces

Provided herein is a system for electrostatic deposition of particles upon a charged substrate to form a coating on a surface of the substrate, the system comprising: an expansion nozzle that releases coating particles having a first average electric potential suspended in a gaseous phase from a near-critical or supercritical fluid that is expanded through the nozzle; and an auxiliary emitter that generates a stream of charged ions having a second average potential in an inert carrier gas; whereby the coating particles interact with the charged ions and the carrier gas to enhance a charge differential between the coating particles and the substrate.

Provided herein is a system for electrostatic deposition of particles upon a charged substrate to form a coating on a surface of the substrate, the system comprising: an expansion nozzle that releases coating particles having a first average electric potential suspended in a gaseous phase from a near-critical or supercritical fluid that is expanded through the nozzle; and an auxiliary emitter that generates a stream of charged ions having a second average electric potential in an inert carrier gas; whereby the coating particles interact with the charged ions and the carrier gas to enhance a potential differential between the coating particles and the substrate.

In some embodiments, the coating particles have a first velocity upon release of the coating particles from the expansion nozzle that is less than a second velocity of the coating particles when the coating particles impact the substrate. In some embodiments, attraction of the coating particles to the substrate is increased as compared to attraction of the coating particles to the substrate in a system without the auxiliary emitter.

In some embodiments, the first average electric potential is different than the second average electric potential. In some embodiments, an absolute value of the first average electric potential is less than an absolute value of the second average electric potential, and wherein a polarity the charged ions is the same as a polarity of the coating particles.

In some embodiments, the auxiliary emitter comprises an electrode having a tapered end that extends into a gas channel that conducts the stream of charged ions in the inert carrier gas toward the charged coating particles. In some embodiments, the auxiliary emitter further comprises a capture electrode. In some embodiments, the auxiliary emitter comprises a metal rod with a tapered tip and a delivery orifice.

In some embodiments, the substrate is positioned in a circumvolving orientation around the expansion nozzle.

In some embodiments, the substrate comprises a conductive material. In some embodiments, the substrate comprises a semi-conductive material. In some embodiments, the substrate comprises a polymeric material.

In some embodiments, the charged ions at the second electric potential are a positive corona or a negative corona positioned between the expansion nozzle and the substrate. In some embodiments, the charged ions at the second electric potential are a positive corona or a negative corona positioned between the auxiliary emitter and the substrate.

In some embodiments, the coating particles comprises at least one of: polylactic acid (PLA); poly(lactic-co-glycolic acid) (PLGA); polycaprolactone (poly(e-caprolactone)) (PCL), polyglycolide (PG) or (PGA), poly-3-hydroxybutyrate; LPLA poly(l-lactide), DLPLA poly(dl-lactide), PDO poly(dioxolane), PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid) and blends, combinations, homopolymers, condensation polymers, alternating, block, dendritic, crosslinked, and copolymers thereof.

In some embodiments, the coating particles comprise at least one of: polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly (styrene-b-isobutylene-b-styrene), poly-butyl methacrylate, poly-byta-diene, and blends, combinations, homopolymers, condensation polymers, alternating, block, dendritic, crosslinked, and copolymers thereof.

In some embodiments, the coating particles include a drug comprising one or more of: rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 40-O-(6-Hydroxy)hexyl-rapamycin 40-O-[2-(2-Hydroxy)ethoxy]ethyl-rapamycin 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-

Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, isomers, racemates, diastereoisomers, prodrugs, hydrate, ester, or analogs thereof.

In some embodiments, the coating particles have a size between about 0.01 micrometers and about 10 micrometers.

In some embodiments, the second velocity is in the range from about 0.1 cm/sec to about 100 cm/sec. In some embodiments, the coating has a density on the surface in the range from about 1 volume % to about 60 volume %.

In some embodiments, the coating is a multilayer coating. In some embodiments, the substrate is a medical implant. In some embodiments, the substrate is an interventional device. In some embodiments, the substrate is a diagnostic device. In some embodiments, the substrate is a surgical tool. In some embodiments, the substrate is a stent.

Medical implants may comprise any implant for insertion into the body of a human or animal subject, including but not limited to stents (e.g., coronary stents, vascular stents including peripheral stents and graft stents, urinary tract stents, urethral/prostatic stents, rectal stent, oesophageal stent, biliary stent, pancreatic stent), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc. In some embodiments, the substrate is selected from the group consisting of: stents, joints, screws, rods, pins, plates, staples, shunts, clamps, clips, sutures, suture anchors, electrodes, catheters, leads, grafts, dressings, pacemakers, pacemaker housings, cardioverters, cardioverter housings, defibrillators, defibrillator housings, prostheses, ear drainage tubes, ophthalmic implants, orthopedic devices, vertebral disks, bone substitutes, anastomotic devices, perivascular wraps, colostomy bag attachment devices, hemostatic barriers, vascular implants, vascular supports, tissue adhesives, tissue sealants, tissue scaffolds and intraluminal devices.

In some embodiments, the substrate is an interventional device. An "interventional device" as used herein refers to any device for insertion into the body of a human or animal subject, which may or may not be left behind (implanted) for any length of time including, but not limited to, angioplasty balloons, cutting balloons.

In some embodiments, the substrate is a diagnostic device. A "diagnostic device" as used herein refers to any device for insertion into the body of a human or animal subject in order to diagnose a condition, disease or other of the patient, or in order to assess a function or state of the body of the human or animal subject, which may or may not be left behind (implanted) for any length of time.

In some embodiments, the substrate is a surgical tool. A "surgical tool" as used herein refers to a tool used in a medical procedure that may be inserted into (or touch) the body of a human or animal subject in order to assist or participate in that medical procedure.

In some embodiments, the coating is non-dendritic as compared to a baseline average coating thickness. In some embodiments, no coating extends more than 0.5 microns from the baseline average coating thickness. In some embodiments, no coating extends more than 1 micron from the baseline average coating thickness.

In some embodiments, the coating is non-dendritic such that there is no surface irregularity of the coating greater than 0.5 microns. In some embodiments, the coating is non-dendritic such that there is no surface irregularity of the coating greater than 1 micron. In some embodiments, the coating is non-dendritic such that there is no surface irregularity of the coating greater than 2 microns following sintering of the coated substrate. In some embodiments, the coating is non-dendritic such that there is no surface irregularity of the coating greater than 3 microns following sintering of the coated substrate.

FIG. 4 shows an exemplary e-RESS system 200 for coating substrates including, e.g., medical device substrates and associated surfaces, according to an embodiment of the invention. Auxiliary emitter 100 mounts at a preselected location to deposition vessel 30. Inert carrier gas (e.g., dry nitrogen) flowed through auxiliary emitter 100 carries charged ions generated by auxiliary emitter 100 into deposition vessel 30. Auxiliary emitter 100 can be positioned at any location that provides a maximum generation of charged ions to deposition vessel 30 and further facilitates convenient operation including, but not limited to, e.g., external (e.g., top, side) and internal. No limitations are intended. In some embodiments, auxiliary emitter 100 is mounted at the top of deposition vessel 30 to maximize charge delivered thereto. Auxiliary emitter 100 delivers charged ions that supplements charge of solute particles released from expansion nozzle orifice 36 into deposition vessel 30. A typical voltage applied to stents 34 (substrates) is −15 kV, but is not limited thereto. In some embodiments, metal (copper) sheath 42 is grounded, but operation is not limited thereto. In some embodiments, polarity of the at least one substrate is a negative polarity and charge of the solid solute particles is enhanced (supplemented) with a positive charge. In another embodiment, the polarity of the at least one substrate is a positive polarity and the charge of the solid solute particles is enhanced (supplemented) with a negative charge. In deposition vessel 30, expansion nozzle assembly 32 (containing a $1^{st}$ e-RESS electrode 44 or metal sheath 44) is located at the center of rotating stage 40 to which metal stents 34 (collectively a $2^{nd}$ e-RESS electrode 34) are mounted so as to be coated in the coating process, as described further herein. A typical voltage applied to stents 34 (substrates) is −15 kV, but is not limited thereto. In some embodiments, metal (copper) sheath 44 of expansion assembly 32 is grounded, but operation is not limited thereto. In some embodiments, polarity of the polarity of the metal stents 34 or substrates 34 is a negative polarity and charge of the solid coating particles is enhanced (i.e., supplemented) with, e.g., a positive charge. In another embodiment, polarity of the metal stents 34 or substrates 34 is a positive polarity and the charge of the solid coating particles is enhanced (i.e., supplemented) with, e.g., a negative charge. No limitations are intended.

Process for Coating Substrates and Surfaces

Provided herein is a process for forming a coating on a surface of a substrate, comprising: establishing an electric field between the substrate and a counter electrode; producing coating particles suspended in a gaseous phase of an expanded near-critical or supercritical fluid having an first average electric potential; and contacting the coating particles with a stream of charged ions at a second average potential in an inert carrier gas to increase the charge differential between the coating particles and the substrate.

Provided herein is a method for coating a surface of a substrate with a preselected material forming a coating, comprising the steps of: establishing an electric field between the substrate and a counter electrode; producing coating particles suspended in a gaseous phase of an expanded near-critical or supercritical fluid having an first average electric potential; and contacting the coating particles with a stream of charged ions at a second average potential in an inert carrier gas to increase the potential differential between the coating particles and the substrate.

In some embodiments, the coating particles have a first velocity upon release of the coating particles from the expansion nozzle that is less than a second velocity of the coating particles when the coating particles impact the substrate. In some embodiments, attraction of the coating particles to the substrate is increased as compared to attraction of the coating particles to the substrate in a system without the auxiliary emitter. In some embodiments, the first average electric potential is different than the second average electric potential. In some embodiments, an absolute value of the first average electric potential is less than an absolute value of the second average electric potential, and wherein a polarity the charged ions is the same as a polarity of the coating particles.

In some embodiments, the coating particles have a size between about 0.01 micrometers and about 10 micrometers.

In some embodiments, the substrate has a negative polarity and an enhanced charge of the coating particles following the contacting step is a positive charge; or wherein the substrate has a positive polarity and an enhanced charge of the coating particles following the contacting step is a negative charge.

In some embodiments, the contacting step comprises forming a positive corona or forming a negative corona positioned between the expansion nozzle and the substrate. In some embodiments, the contacting step comprises forming a positive corona or forming a negative corona positioned between the auxiliary emitter and the substrate In some embodiments, the coating has a density on the surface from about 1 volume % to about 60 volume %.

In some embodiments, the coating particles comprises at least one of: a polymer, a drug, a biosorbable material, a protein, a peptide, and a combination thereof.

In some embodiments, the coating particles comprises at least one of: polylactic acid (PLA); poly(lactic-co-glycolic acid) (PLGA); polycaprolactone (poly(e-caprolactone)) (PCL), polyglycolide (PG) or (PGA), poly-3-hydroxybutyrate; LPLA poly(l-lactide), DLPLA poly(dl-lactide), PDO poly(dioxolane), PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid) and blends, combinations, homopolymers, condensation polymers, alternating, block, dendritic, crosslinked, and copolymers thereof. In some embodiments, the coating on the substrate comprises polylactoglycolic acid (PLGA) at a density greater than 5 volume %.

In some embodiments, the coating particles polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene-C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-byta-diene, and blends, combinations, homopolymers, condensation polymers, alternating, block, dendritic, crosslinked, and copolymers thereof.

In some embodiments, the coating particles include a drug comprising one or more of: rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 40-O-(6-Hydroxy)hexyl-rapamycin 40-O-[2-(2-Hydroxy)ethoxy]ethyl-rapamycin 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, isomers, racemates, diastereoisomers, prodrugs, hydrate, ester, or analogs thereof.

In some embodiments, the method further includes the step of sintering the coating at a temperature in the range from about 25° C. to about 150° C. to form a dense, thermally stable film on the surface of the substrate.

In some embodiments, the method further includes the step of sintering the coating in the presence of a solvent gas to form the dense, thermally stable film on the surface of the substrate.

In some embodiments, the producing and the contacting steps, at least, are repeated to form a multilayer film.

In some embodiments, the substrate is at least a portion of a medical implant. In some embodiments, the substrate is an interventional device. In some embodiments, the substrate is a diagnostic device. In some embodiments, the substrate is a surgical tool. In some embodiments, the substrate is a stent. In some embodiments, the substrate is a medical balloon.

Medical implants may comprise any implant for insertion into the body of a human or animal subject, including but not limited to stents (e.g., coronary stents, vascular stents including peripheral stents and graft stents, urinary tract stents, urethral/prostatic stents, rectal stent, oesophageal stent, biliary stent, pancreatic stent), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc. In some embodiments, the substrate is selected from the group consisting of: stents, joints, screws, rods, pins, plates, staples, shunts, clamps, clips, sutures, suture anchors, electrodes, catheters, leads, grafts, dressings, pacemakers, pacemaker housings, cardioverters, cardioverter housings, defibrillators, defibrillator housings, prostheses, ear drainage tubes, ophthalmic implants, orthopedic devices, vertebral disks, bone substitutes, anastomotic devices, perivascular wraps, colostomy bag attachment devices, hemostatic barriers, vascular implants, vascular supports, tissue adhesives, tissue sealants, tissue scaffolds and intraluminal devices.

In some embodiments, the substrate is an interventional device. An "interventional device" as used herein refers to any device for insertion into the body of a human or animal subject, which may or may not be left behind (implanted) for any length of time including, but not limited to, angioplasty balloons, cutting balloons.

In some embodiments, the substrate is a diagnostic device. A "diagnostic device" as used herein refers to any device for insertion into the body of a human or animal subject in order to diagnose a condition, disease or other of the patient, or in order to assess a function or state of the body of the human or animal subject, which may or may not be left behind (implanted) for any length of time.

In some embodiments, the substrate is a surgical tool. A "surgical tool" as used herein refers to a tool used in a medical procedure that may be inserted into (or touch) the body of a human or animal subject in order to assist or participate in that medical procedure.

In some embodiments, the coating is non-dendritic as compared to a baseline average coating thickness. In some embodiments, no coating extends more than 0.5 microns from the baseline average coating thickness. In some embodiments, no coating extends more than 1 micron from the baseline average coating thickness.

In some embodiments, the coating is non-dendritic such that there is no surface irregularity of the coating greater than 0.5 microns. In some embodiments, the coating is non-dendritic such that there is no surface irregularity of the coating greater than 1 micron. In some embodiments, the coating is non-dendritic such that there is no surface irregularity of the coating greater than 2 microns following sintering of the coated substrate. In some embodiments, the coating is non-dendritic such that there is no surface irregularity of the coating greater than 3 microns following sintering of the coated substrate.

Figure 5:
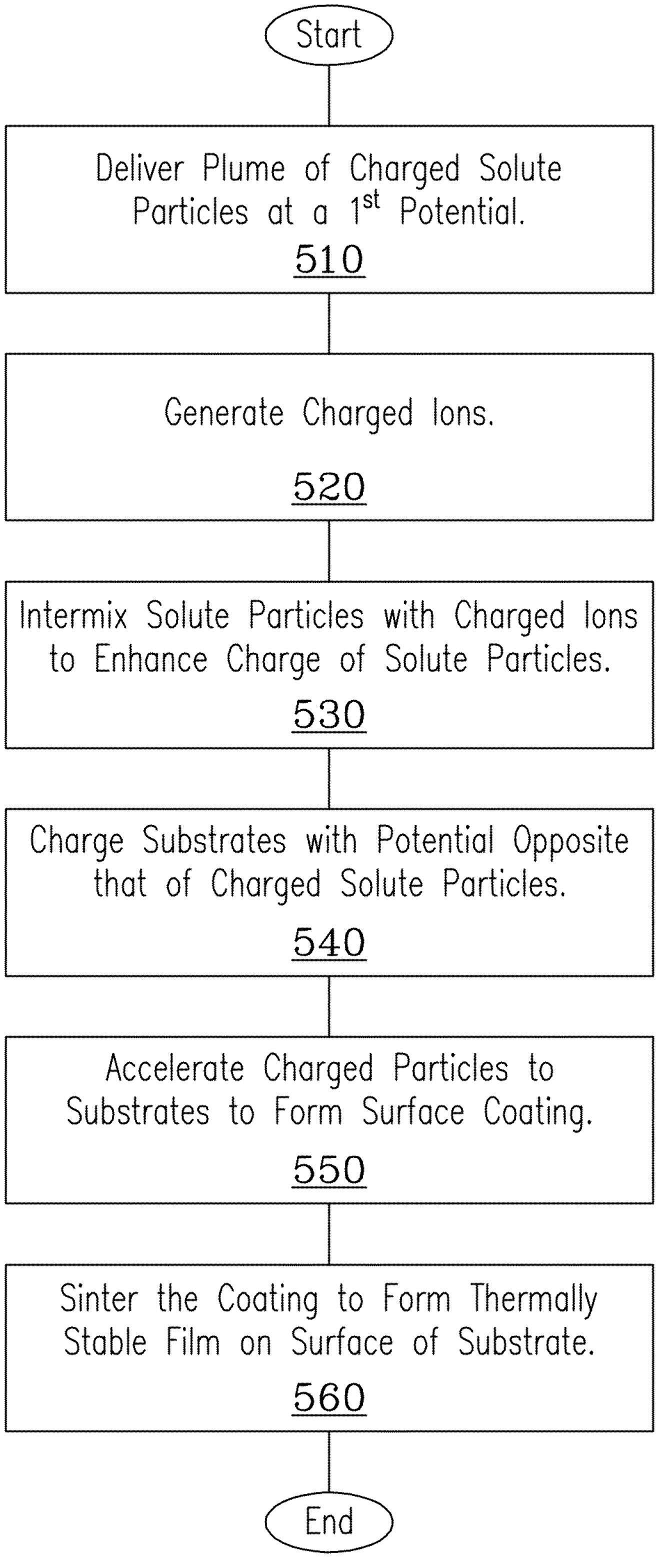
FIG. 5 shows exemplary process steps for coating a substrate, according to an embodiment of the process of the invention.

FIG. 5 shows exemplary process steps for coating substrates with a low dendricity coating, according to an embodiment of the e-RESS process of the invention. {START}. In one step {step 510}, solid solute (coating) particles are produced by rapid expansion of supercritical solution (or near-critical) solution (RESS). The coating particles are released at least partially charged having an average electric potential as a consequence of the interaction between the expanding solution and the nucleating solute particles within the walls of the expansion nozzle assembly 32. The particles are released in a plume of the expansion gas. Aspects of the RESS expansion process for generating coating particles including, but not limited to, e.g., solutes (coating materials), solvents, temperatures, pressures, and voltages, and sintering (e.g., gas and/or heat sintering) to form stable thin films are detailed in U.S. Pat. Nos. 4,582,731; 4,734,227; 4,734,451; 6,756,084; and 6,749,902, which references are incorporated herein in their entirety. In typical operation, RESS parameters include an operating temperature of ~150° C. and a pressure of up to 5500 psi for releasing the super-critical or near-critical solution are used. In another step {step 520}, charged ions are generated and used to enhance (supplement) charge of the coating particles. In another step {step 530}, charged ions are delivered in an inert flow gas from the auxiliary emitter (FIG. 2) and delivered into the deposition vessel (FIG. 4) where the charged ions intermix with the charged coating particles released from the RESS expansion nozzle (FIG. 3). The auxiliary emitter delivers a corona of charge that is either positive or negative. The charged ions in the corona deliver their charge (+ or −) to the coating particles, thereby enhancing (supplementing) the charge of the coating particles. The charged coating particles (e.g., with enhanced positive or enhanced negative) are then preferentially collected on selected substrates to which an opposite (e.g., negative for positive; or positive for negative) high voltage (polarity) is applied, or vice versa. In another step {step 540}, a potential difference is established between a first e-RESS electrode 44 in expansion nozzle assembly 32 and the substrates (stents) 34 that collectively act as a second e-RESS electrode 34. The substrates are positioned at a suitable location, e.g., equidistant from or adjacent to, electrode 44 of RESS assembly 32 to establish a suitable electric field between the two e-RESS electrodes 34, 44. The potential difference generates an electric field between the two e-RESS electrodes 34, 44. In some embodiments, the stents 34 are charged with a high potential (e.g., 15 kV, positive or negative); RESS assembly 32 electrode 44 (FIG. 3) is grounded, acting as a proximal ground electrode 44. In an alternate configuration, high voltage is applied to the proximal electrode 44 (e.g., metal sheath 44 of the expansion assembly 32), and the stents 34 (acting as a $2^{nd}$ e-RESS electrode 34) are grounded, establishing a potential difference between the two e-RESS electrodes 34, 44. Either electrode 34, 44 can have an opposite potential applied, or vice versa. No limitations are intended by the exemplary implementations. Substrates (stents) are charged, e.g., using an independent power supply (not shown), or another charging device as will be understood by those of ordinary skill in the electrical arts. No limitations are intended. In another step (step 550), coating particles now supplemented with enhanced charge (e.g., with enhanced positive or enhanced negative) experience an increased attraction to an oppositely charged substrate, and are accelerated through the electric field between the RESS electrodes at the selected potential. The impact velocity of the coating particles increases the impact energy at the surface of the charged substrate, forming a dense and/or uniform coating on the surface of the substrate. The enhanced charge on the particles enhances the collection (deposition) efficiency of the particles on the substrates. The enhanced charge and impact velocity of the charged coating particles improves the microstructure of the coating on the surface, minimizing the dendricity of the collected material deposited to the substrate, thereby increasing and improving the coating density as well as the uniformity of the coatings deposited to the substrate surface. In another step {step 560}, sintering of the coating forms a dense, thermally stable film on the substrate. Sintering can be performed by heating the substrates using various temperatures (so-called "heat sintering") and/or sintering the substrates with a gaseous solvent phase to reduce the sintering temperatures used (so-called "gas sintering"). Temperatures for sintering of the coating may be selected in the range from about 25° C. to about 150° C., but temperatures are not intended to be limiting. Sintered films include, but are not limited to, e.g., single layer films and multilayer films. For example, substrates (e.g., stents) or medical devices staged within the deposition vessel can be coated with a single layer of a selected material, e.g., a polymer, a drug, and/or another material. Or, various multilayer films can be formed by some embodiment processes of the invention, as described further herein (END).

Particle Size

Charged coating particles used in some embodiments have a size (cross-sectional diameter) between about 10 nm (0.01 μm) and 10 μm. More particularly, coating particles have a size selected between about 10 nm (0.01 μm) and 2 μm.

Velocities of spherical particles in an electrical field (E) carrying maximum charge (q) can be determined from equations detailed, e.g., in "Charging of Materials and Transport of Charged Particles" (Wiley Encyclopedia of Electrical and Electronics Engineering, John G. Webster (Editor), Volume 7, 1999, John Wiley & Sons, Inc., pages 20-24), and "Properties, Behavior, and Measurement of Airborne Particles" (Aerosol Technology, William C. Hinds, 1982, John Wiley & Sons, Inc., pages 284-314), which references are incorporated herein. In particular, the electrostatic force (F) on a particle in an electric field (E) is given by Equation [1], as follows:

$$F=qE \qquad [1]$$

Here, (q) is the electric charge [SI units: Coulombs] on the particle in the electric field (E) [SI units: Newtons per Coulomb ($N\cdot C^{-1}$)], which experiences an electrostatic force (F).

A particle also experiences a viscous drag force ($F_d$) in an enclosure gas, which is given by Equation [2], as follows:

$$F_d=6\pi\mu RV \qquad [2]$$

Here, (ρ) is the dynamic (absolute) viscosity of the selected gas, [e.g., as listed in "Viscosity of Gases", CRC Handbook of Chemistry and Physics, $71^{st}$ ed., CRC Press, Inc., 1990-1991, page 6-140, incorporated herein] at the selected gas temperature and pressure [SI units: Pascal seconds (Pa·s), where 1 $\mu Pa\cdot s=10^{-5}$ poise; (R) is the radius of the particle (SI units: meters); and (V) is the particle terminal velocity [SI units: meters per second, ($m\cdot s^{-1}$)]. Viscosities of pure gases can vary by as much as a factor of 5 depending upon the gas type. Viscosities of refrigerant gases (e.g., fluorocarbon refrigerants) can be determined using a corresponding states method detailed, e.g., by Klein et al. [in Int. J. Refrigeration 20: 208-217, 1997, incorporated herein] over a temperature range from about −31.2° C. to 226.9° C. and pressures up to about 600 atm. Viscosities of mixed gases can be determined using Chapman-Enskog theory detailed, e.g., in ["The Properties of Gases and Liquids", $5^{th}$ ed., 2001, McGraw-Hill, Chapter 9, pages 9.1-9.51, incorporated herein], which viscosities are non-linear functions of the mole fractions of each pure gas. An exemplary e-RESS solvent used herein comprising fluoropropane refrigerant (e.g., R-236ea, Dyneon, Oakdale, Minn., USA) has a typical viscosity [at a pressure of 1 bar (15 psia), and temperature of 300K] of about −11.02 μPa·sec; nitrogen ($N_2$) gas used as a typical carrier gas for the auxiliary emitter of the invention has a viscosity [at a pressure of 1 bar (15 psia), and temperature of 300K] of about −17.89 μPa·sec. Viscosity of an exemplary mixed gas [R-236ea and $N_2$] (see Example 1) was estimated at −14.5 μPa·sec. The e-RESS solvent gas [R-236ea] demonstrated a viscosity about 40% lower than the $N_2$ carrier gas in the enclosure chamber.

The terminal velocity (V) of charged particles in an electric field (E) can thus be determined by calculation by equating the electrostatic force (F) and the viscous drag force ($F_d$) exerted on a particle moving through a gas, as given by Equation [3]:

$$V=\frac{qE}{6\pi\mu R} \qquad [3]$$

Maximum terminal velocities for particles may also be determined from reference tables known in the art that include data based on the maximum possible charge on a particle and the maximum potentials achievable based on gas breakdown potentials in a selected gas.

Terminal velocities of particles released in the RESS expansion plume depend at least in part on the diameter of the particles produced. For example, coating particles having a size (diameter) of about 0.2 μm have an expected terminal (impact) velocity of from about 0.1 cm/sec to about 1 cm/sec [see, e.g., Table 4, "Charging of Materials and Transport of Charged Particles", Wiley Encyclopedia of Electrical and Electronics Engineering, Volume 7, 1999, John G. Webster (Editor), John Wiley & Sons, Inc., page 23]. Coating particles with a size of about 2 μm have an expected terminal (impact) velocity of about 1 cm/sec to about 10 cm/sec, but velocities are not limited thereto. For example, in various embodiments, charged coating particles will have expected terminal (impact) velocities at least from about 0.1 cm/sec to about 100 cm/sec. Thus, no limitations are intended.

Applications

Coatings produced by of some embodiments can be deposited to various substrates and devices, including, e.g., medical devices and other components, e.g., for use in biomedical applications. Substrates can comprise materials including, but not limited to, e.g., conductive materials, semi-conductive materials, polymeric materials, and other selected materials. In various embodiments, coatings can be applied to medical stent devices. In other embodiments, substrates can be at least a portion of a medical device, e.g., a medical balloon, e.g., a non-conductive polymer balloon. All applications as will be considered by those of skill in the art in view of the disclosure are within the scope of the invention. No limitations are intended.

Coating Materials

Coating particles prepared by some embodiments can include various materials selected from, e.g., polymers, drugs, biosorbable materials, bioactive proteins and peptides, as well as combinations of these materials. These materials find use in coatings that are applied to, e.g., medical devices (e.g., medical balloons) and medical implant devices (e.g., drug-eluting stents), but are not limited thereto. Choice for near-critical or supercritical fluid is based on the solubility of the selected solute(s) of interest, which is not limited.

Polymers used in conjunction in some embodiments include, but are not limited to, e.g., polylactoglycolic acid (PLGA); polyethylene vinyl acetate (PEVA); poly(butyl methacrylate) (PBMA); perfluorooctanoic acid (PFOA); tetrafluoroethylene (TFE); hexafluoropropylene (HFP); polylactic acid (PLA); polyglycolic acid (PGA), including combinations of these polymers. Other polymers include various mixtures of tetrafluoroethylene, hexafluoropropylene, and vinylidene fluoride (e.g., THV) at varying molecular ratios (e.g., 1:1:1).

Biosorbable polymers used in conjunction in some embodiments include, but are not limited to, e.g., polylactic acid (PLA); poly(lactic-co-glycolic acid) (PLGA); polycaprolactone (poly(e-caprolactone)) (PCL), polyglycolide (PG) or (PGA), poly-3-hydroxybutyrate; LPLA poly(l-lactide), DLPLA poly(dl-lactide), PDO poly(dioxolane), PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy) propane-co-sebacic acid) and blends, combinations, homopolymers, condensation polymers, alternating, block, dendritic, crosslinked, and copolymers thereof.

Durable (biostable) polymers used in some embodiments include, but are not limited to, e.g., polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), polybutyl methacrylate, poly-byta-diene, and blends, combinations, homopolymers, condensation polymers, alternating, block, dendritic, crosslinked, and copolymers thereof. Other polymers selected for use can include polymers to which drugs are chemically (e.g., ionically and/or covalently) attached or otherwise mixed, including, but not limited to, e.g., heparin-containing polymers (HCP).

Drugs used in embodiments described herein include, but are not limited to, e.g., antibiotics (e.g., Rapamycin [CAS No. 53123-88-9], LC Laboratories, Woburn, Mass., USA, anticoagulants (e.g., Heparin [CAS No. 9005-49-6]; antithrombotic agents (e.g., clopidogrel); antiplatelet drugs (e.g., aspirin); immunosuppressive drugs; antiproliferative drugs; chemotherapeutic agents (e.g., paclitaxel also known by the trade name TAXOL® [CAS No. 33069-62-4], Bristol-Myers Squibb Co., New York, N.Y., USA) and/or a prodrug, a derivative, an analog, a hydrate, an ester, and/or a salt thereof).

Antibiotics include, but are not limited to, e.g., amikacin, amoxicillin, gentamicin, kanamycin, neomycin, netilmicin, paromomycin, tobramycin, geldanamycin, herbimycin, carbacephem (loracarbef), ertapenem, doripenem, imipenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, clarithromycin, clavulanic acid, clindamycin, teicoplanin, azithromycin, dirithromycin, erythromycin, troleandomycin, telithromycin, aztreonam, ampicillin, azlocillin, bacampicillin, carbenicillin, cloxacillin, dicloxacillin, flucloxacillin, mezlocillin, meticillin, nafcillin, norfloxacin, oxacillin, penicillin-G, penicillin-V, piperacillin, pvampicillin, pivmecillinam, ticarcillin, bacitracin, colistin, polymyxin-B, ciprofloxacin, enoxacin, gatifloxacin, levofloxacin, lomefloxacin, moxifloxacin, ofloxacin, trovafloxacin, grepafloxacin, sparfloxacin, afenide, prontosil, sulfacetamide, sulfamethizole, sulfanilimide, sulfamethoxazole, sulfisoxazole, trimethoprim, trimethoprim-sulfamethoxazole, demeclocycline, doxycycline, oxytetracycline, tetracycline, arsphenamine, chloramphenicol, lincomycin, ethambutol, fosfomycin, furazolidone, isoniazid, linezolid, mupirocin, nitrofurantoin, platensimycin, pyrazinamide, quinupristin/dalfopristin, rifampin, thiamphenicol, rifampicin, minocycline, sultamicillin, sulbactam, sulphonamides, mitomycin, spectinomycin, spiramycin, roxithromycin, and meropenem.

Antibiotics can also be grouped into classes of related drugs, for example, aminoglycosides (e.g., amikacin, gentamicin, kanamycin, neomycin, netilmicin, paromomycin, streptomycin, tobramycin), ansamycins (e.g., geldanamycin, herbimycin), carbacephem (loracarbef) carbapenems (e.g., ertapenem, doripenem, imipenem, meropenem), first generation cephalosporins (e.g., cefadroxil, cefazolin, cefalotin, cefalexin), second generation cephalosporins (e.g., cefaclor, cefamandole, cefoxitin, cefprozil, cefuroxime), third generation cephalosporins (e.g., cefixime, cefdinir, cefditoren, cefoperazone, cefotaxime, cefpodoxime, ceftazidime, ceftibuten, ceftizoxime, ceftriaxone), fourth generation cephalosporins (e.g., cefepime), fifth generation cephalosporins (e.g., ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, bacampicillin, carbenicillin, cloxacillin, dicloxacillin, flucloxacillin, mezlocillin, meticillin, nafcillin, oxacillin, penicillins-G and -V, piperacillin, pvampicillin, pivmecillinam, ticarcillin), polypeptides (e.g., bacitracin, colistin, polymyxin-B), quinolones (e.g., ciprofloxacin, enoxacin, gatifloxacin, levofloxacin, lomefloxacin, moxifloxacin, norfloxacin, ofloxacin, trovafloxacin, grepafloxacin, sparfloxacin, trovafloxacin), sulfonamides (e.g., afenide, prontosil, sulfacetamide, sulfamethizole, sulfanilimide, sulfasalazine, sulfamethoxazole, sulfisoxazole, trimethoprim, trimethoprim-sulfamethoxazole), tetracyclines (e.g., demeclocycline, doxycycline, minocycline, oxytetracycline, tetracycline).

Anti-thrombotic agents (e.g., clopidogrel) are contemplated for use in the methods and devices described herein. Use of anti-platelet drugs (e.g., aspirin), for example, to prevent platelet binding to exposed collagen, is contemplated for anti-restenotic or anti-thrombotic therapy. Anti-platelet agents include “GpIIb/IIIa inhibitors” (e.g., abciximab, eptifibatide, tirofiban, RheoPro) and “ADP receptor blockers” (prasugrel, clopidogrel, ticlopidine). Particularly useful for local therapy are dipyridamole, which has local vascular effects that improve endothelial function (e.g., by causing local release of t-PA, that will break up clots or prevent clot formation) and reduce the likelihood of platelets and inflammatory cells binding to damaged endothelium, and cAMP phosphodiesterase inhibitors, e.g., cilostazol, that could bind to receptors on either injured endothelial cells or bound and injured platelets to prevent further platelet binding.

Chemotherapeutic agents include, but are not limited to, e.g., angiostatin, DNA topoisomerase, endostatin, genistein, ornithine decarboxylase inhibitors, chlormethine, melphalan, pipobroman, triethylene-melamine, triethylenethiophosphoramine, busulfan, carmustine (BCNU), streptozocin, 6-mercaptopurine, 6-thioguanine, Deoxyco-formycin, IFN-$\alpha$, 17$\alpha$-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, estramustine, medroxyprogesteroneacetate, flutamide, zoladex, mitotane, hexamethylmelamine, indolyl-3-glyoxylic acid derivatives, (e.g., indibulin), doxorubicin and idarubicin, plicamycin (mithramycin) and mitomycin, mechlorethamine, cyclophosphamide analogs, trazenes—dacarbazinine (DTIC), pentostatin and 2-chlorodeoxyadenosine, letrozole, camptothecin (and derivatives), navelbine, erlotinib, capecitabine, acivicin, acodazole hydrochloride, acronine, adozelesin, aldesleukin, ambomycin, ametantrone acetate, anthramycin, asperlin, azacitidine, azetepa, azotomycin, batimastat, benzodepa, bisnafide, bisnafide dimesylate, bizelesin, bropirimine, cactinomycin, calusterone, carbetimer, carubicin hydrochloride, carzelesin, cedefingol, celecoxib (COX-2 inhibitor), cirolemycin, crisnatol mesylate, decitabine, dexormaplatin, dezaguanine mesylate, diaziquone, duazomycin, edatrexate, eflomithine, elsamitrucin, enloplatin, enpromate, epipropidine, erbulozole, etanidazole, etoprine, flurocitabine, fosquidone, lometrexol, losoxantrone hydrochloride, masoprocol, maytansine, megestrol acetate, melengestrol acetate, metoprine, meturedepa, mitindomide, mitocarcin, mitocromin, mitogillin, mitomalcin, mitosper, mycophenolic acid, nocodazole, nogalamycin, ormaplatin, oxisuran, pegaspargase, peliomycin, pentamustine, perfosfamide, piposulfan, plomestane, porfimer sodium, porfiromycin, puromycin, pyrazofurin, riboprine, safingol, simtrazene, sparfosate sodium, spiromustine, spiroplatin, streptonigrin, sulofenur, tecogalan sodium, taxotere, tegafur, teloxantrone hydrochloride, temoporfin, thiamiprine, tirapazamine, trestolone acetate, triciribine phosphate, trimetrexate glucuronate, tubulozole hydrochloride, uracil mustard, uredepa, verteporfin, vinepidine sulfate, vinglycinate sulfate, vinleurosine sulfate, vinorelbine tartrate, vinrosidine sulfate, zeniplatin, zinostatin, 20-epi-1,25 dihydroxyvitamin-D3, 5-ethynyluracil, acylfulvene, adecypenol, ALL-TK antagonists, ambamustine, amidox, amifostine, aminolevulinic acid, amrubicin, anagrelide, andrographolide, antagonist-D, antagonist-G, antarelix, anti-dorsalizing morphogenetic protein-1, antiandrogen, antiestrogen, estrogen agonist, apurinic acid, ara-CDP-DL-PTBA, arginine deaminase, asulacrine, atamestane, atrimustine, axinastatin-1, axinastatin-2, axinastatin-3, azasetron, azatoxin, azatyrosine, baccatin III derivatives, balanol, BCR/ABL antagonists, benzochlorins, benzoylstaurosporine, beta lactam derivatives, beta-alethine, betaclamycin-B, betulinic acid, bFGF inhibitor, bisaziridinyispermine, bistratene-A, breflate, buthionine suffoximine, calcipotriol, calphostin-C, carboxamide-amino-triazole, carboxyamidotriazole, CaRest M3, CARN 700, cartilage derived inhibitor, casein kinase inhibitors (ICOS), castanospermine, cecropin B, cetrorelix, chloroquinoxaline sulfonamide, cicaprost, cis-porphyrin, clomifene analogues, clotrimazole, collismycin-A, collismycin-B, combretastatin-A4, combretastatin analogue, conagenin, crambescidin-816, cryptophycin-8, cryptophycin-A derivatives, curacin-A, cyclopentanthraquinones, cycloplatam, cypemycin, cytolytic factor, cytostatin, dacliximab, dehydrodidemnin B, dexamethasone, dexifosfamide, dexrazoxane, dexverapamil, didemnin-B, didox, diethylnorspermine, dihydro-5-azacytidine, dihydrotaxol, 9-, dioxamycin, docosanol, dolasetron, dronabinol, duocarmycin-SA, ebselen, ecomustine, edelfosine, edrecolomab, elemene, emitefur, estramustine analogue, filgrastim, flavopiridol, flezelastine, fluasterone, fluorodaunorunicin hydrochloride, forfenimex, gadolinium texaphyrin, galocitabine, gelatinase inhibitors, glutathione inhibitors, hepsulfam, heregulin, hexamethylene bisacetamide, hypericin, ibandronic acid, idramantone, ilomastat, imatinib (e.g., Gleevec), imiquimod, immunostimulant peptides, insulin-like growth factor-1 receptor inhibitor, interferon agonists, interferons, interleukins, iobenguane, iododoxorubicin, ipomeanol, 4-, iroplact, irsogladine, isobengazole, isohomohalicondrin-B, itasetron, jasplakinolide, kahalalide-F, lamellarin-N triacetate, leinamycin, lenograstim, lentinan sulfate, leptolstatin, leukemia inhibiting factor, leukocyte alpha interferon, leuprolide+estrogen+progesterone, linear polyamine analogue, lipophilic disaccharide peptide, lipophilic platinum compounds, lissoclinamide-7, lobaplatin, lombricine, loxoribine, lurtotecan, lutetium texaphyrin, lysofylline, lytic peptides, maitansine, mannostatin-A, marimastat, maspin, matrilysin inhibitors, matrix metalloproteinase inhibitors, meterelin, methioninase, metoclopramide, MIF inhibitor, mifepristone, miltefosine, mirimostim, mitoguazone, mitotoxin fibroblast growth factor-saporin, mofarotene, molgramostim, Erbitux, human chorionic gonadotrophin, monophosphoryl lipid A+myobacterium cell wall sk, mustard anticancer agent, mycaperoxide-B, mycobacterial cell wall extract, myriaporone, N-acetyldinaline, N-substituted benzamides, nagrestip, naloxone+pentazocine, napavin, naphterpin, nartograstim, nedaplatin, nemorubicin, neridronic acid, nisamycin, nitric oxide modulators, nitroxide antioxidant, nitrullyn, oblimersen (Genasense), O6-benzylguanine, okicenone, onapristone, ondansetron, oracin, oral cytokine inducer, paclitaxel analogues and derivatives, palauamine, palmitoylrhizoxin, pamidronic acid, panaxytriol, panomifene, parabactin, peldesine, pentosan polysulfate sodium, pentrozole, perflubron, perillyl alcohol, phenazinomycin, phenylacetate, phosphatase inhibitors, picibanil, pilocarpine hydrochloride, placetin-A, placetin-B, plasminogen activator inhibitor, platinum complex, platinum compounds, platinum-triamine complex, propyl bis-acridone, prostaglandin-J2, proteasome inhibitors, protein A-based immune modulator, protein kinase-C inhibitors, microalgal, pyrazoloacridine, pyridoxylated hemoglobin polyoxyethylene conjugate, raf antagonists, raltitrexed, ramosetron, ras farnesyl protein transferase inhibitors, ras-GAP inhibitor, retelliptine demethylated, rhenium Re-186 etidronate, ribozymes, RII retinamide, rohitukine, romurtide, roquinimex, rubiginone-B1, ruboxyl, saintopin, SarCNU, sarcophytol A, sargramostim, Sdi-1 mimetics, senescence derived inhibitor-1, signal transduction inhibitors, sizofiran, sobuzoxane, sodium borocaptate, solverol, somatomedin binding protein, sonermin, sparfosic acid, spicamycin-D, splenopentin, spongistatin-1, squalamine, stipiamide, stromelysin inhibitors, sulfinosine, superactive vasoactive intestinal peptide antagonist, suradista, suramin, swainsonine, tallimustine, tazarotene, tellurapyrylium, telomerase inhibitors, tetrachlorodecaoxide, tetrazomine, thiocoraline, thrombopoietin, thrombopoietin mimetic, thymalfasin, thymopoietin receptor agonist, thymotrinan, thyroid stimulating hormone, tin ethyl etiopurpurin, titanocene bichloride, topsentin, translation inhibitors, tretinoin, triacetyluridine, tropisetron, turosteride, ubenimex, urogenital sinus-derived growth inhibitory factor, variolin-B, velaresol, veramine, verdins, vinxaltine, vitaxin, zanoterone, zilascorb, zinostatin stimalamer, acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine, fludarabine phosphate, N-(2'-furanidyl)-5-fluorouracil, Daiichi Seiyaku FO-152, 5-FU-fibrinogen, isopropyl pyrrolizine, Lilly LY-188011, Lilly LY-264618, methobenzaprim, methotrexate, Wellcome MZPES, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR- 2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromustine, Tanabe Seiyaku TA-077, tauromustine, temozolomide, teroxirone, tetraplatin and trimelamol, Taiho 4181-A, aclarubicin, actinomycin-D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitomycin analogues, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, zorubicin, 5-fluorouracil (5-FU), the peroxidate oxidation product of inosine, adenosine, or cytidine with methanol or ethanol, cytosine arabinoside (also referred to as Cytarabin, araC, and Cytosar), 5-Azacytidine, 2-Fluoroadenosine-5'-phosphate (Fludara, also referred to as FaraA), 2-Chlorodeoxyadenosine, Abarelix, Abbott A-84861, Abiraterone acetate, Aminoglutethimide, Asta Medica AN-207, Antide, Chugai AG-041R, Avorelin, aseranox, Sensus B2036-PEG, buserelin, BTG CB-7598, BTG CB-7630, Casodex, cetrolix, clastroban, clodronate disodium, Cosudex, Rotta Research CR-1505, cytadren, crinone, deslorelin, droloxifene, dutasteride, Elimina, Laval University EM-800, Laval University EM-652, epitiostanol, epristeride, Mediolanum EP-23904, EntreMed 2-ME, exemestane, fadrozole, finasteride, formestane, Pharmacia & Upjohn FCE-24304, ganirelix, goserelin, Shire gonadorelin agonist, Glaxo Wellcome GW-5638, Hoechst Marion Roussel Hoe-766, NCI hCG, idoxifene, isocordoin, Zeneca ICI-182780, Zeneca ICI-118630, Tulane University J015X, Schering Ag J96, ketanserin, lanreotide, Milkhaus LDI-200, letrozol, leuprolide, leuprorelin, liarozole, lisuride hydrogen maleate, loxiglumide, mepitiostane, Ligand Pharmaceuticals LG-1127, LG-1447, LG-2293, LG-2527, LG-2716, Bone Care International LR-103, Lilly LY-326315, Lilly LY-353381-HCI, Lilly LY-326391, Lilly LY-353381, Lilly LY-357489, miproxifene phosphate, Orion Pharma MPV-2213ad, Tulane University MZ-4-71, nafarelin, nilutamide, Snow Brand NKS01, Azko Nobel ORG-31710, Azko Nobel ORG-31806, orimeten, orimetene, orimetine, ormeloxifene, osaterone, Smithkline Beecham SKB-105657, Tokyo University OSW-1, Peptech PTL-03001, Pharmacia & Upjohn PNU-156765, quinagolide, ramorelix, Raloxifene, statin, sandostatin LAR, Shionogi S-10364, Novartis SMT-487, somavert, somatostatin, tamoxifen, tamoxifen methiodide, teverelix, toremifene, triptorelin, TT-232, vapreotide, vorozole, Yamanouchi YM-116, Yamanouchi YM-511, Yamanouchi YM-55208, Yamanouchi YM-53789, Schering AG ZK-1911703, Schering AG ZK-230211, and Zeneca ZD-182780, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston-A10, antineoplaston-A2, antineoplaston-A3, antineoplaston-A5, antineoplaston-AS2-1, Henkel-APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Wamer-Lambert CI-921, Warner-Lambert CI-937, Wamer-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, datelliptinium, DFMO, didemnin-B, dihaematoporphyrin ether, dihydrolenperone dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin, Cell Pathways Exisulind (sulindac sulphone or CP-246), fenretinide, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron, Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Wamer-Lambert PD-115934, Warner-Lambert PD-131141, Pierre Fabre PE-1001, ICRT peptide-D, piroxantrone, polyhaematoporphyrin, polypreic acid, Efamol porphyrin, probimane, procarbazine, proglumide, Invitron protease nexin I, Tobishi RA-700, razoxane, retinoids, R-flurbiprofen (Encore Pharmaceuticals), Sandostatin, Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, selenium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine, vinblastine sulfate, vincristine, vincristine sulfate, vindesine, vindesine sulfate, vinestramide, vinorelbine, vintriptol, vinzolidine, withanolides, Yamanouchi YM-534, Zileuton, ursodeoxycholic acid, Zanosar.

Drugs used in some embodiments described herein include, but are not limited to, e.g., an immunosuppresive drug such as a macrolide immunosuppressive drug, which may comprise one or more of rapamycin, biolimus (biolimus A9), 40-O-(2-Hydroxyethyl)rapamycin (everolimus), 40-O-Benzyl-rapamycin, 40-O-(4'-Hydroxymethyl)benzykrapamycin, 40-O-[4'-(1,2-Dihydroxyethyl)]benzykrapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 40-O-(6-Hydroxy)hexyl-rapamycin 40-O-[2-(2-Hydroxy)ethoxy]ethyl-rapamycin 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, isomers, racemates, diastereoisomers, prodrugs, hydrate, ester, or analogs thereof.

Drugs used in embodiments described herein include, but are not limited to, e.g., Acarbose, acetylsalicylic acid, acyclovir, allopurinol, alprostadil, prostaglandins, amantadine, ambroxol, amlodipine, S-aminosalicylic acid, amitriptyline, atenolol, azathioprine, balsalazide, beclomethasone, betahistine, bezafibrate, diazepam and diazepam derivatives, budesonide, bufexamac, buprenorphine, methadone, calcium salts, potassium salts, magnesium salts, candesartan, carbamazepine, captopril, cetirizine, chenodeoxycholic acid, theophylline and theophylline derivatives, trypsins, cimetidine, clobutinol, clonidine, cotrimoxazole, codeine, caffeine, vitamin D and derivatives of vitamin D, colestyramine, cromoglicic acid, coumarin and coumarin derivatives, cysteine, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxylamine, benzodiazepines, diclofenac, desipramine, econazole, ACE inhibitors, enalapril, ephedrine, epinephrine, epoetin and epoetin derivatives, morphinans, calcium antagonists, modafinil, orlistat, peptide antibiotics, phenytoin, riluzoles, risedronate, sildenafil, topiramate, estrogen, progestogen and progestogen derivatives, testosterone derivatives, androgen and androgen derivatives, ethenzamide, etofenamate, etofibrate, fenofibrate, etofylline, famciclovir, famotidine, felodipine, fentanyl, fenticonazole, gyrase inhibitors, fluconazole, fluarizine, fluoxetine, flurbiprofen, ibuprofen, fluvastatin, follitropin, formoterol, fosfomicin, furosemide, fusidic acid, gallopamil, ganciclovir, gemfibrozil, ginkgo, Saint John's wort, glibenclamide, urea derivatives as oral antidiabetics, glucagon, glucosamine and glucosamine derivatives, glutathione, glycerol and glycerol derivatives, hypothalamus hormones, guanethidine, halofantrine, haloperidol, heparin (and derivatives), hyaluronic acid, hydralazine, hydrochlorothiazide (and derivatives), salicylates, hydroxyzine, imipramine, indometacin, indoramine, insulin, iodine and iodine derivatives, isoconazole, isoprenaline, glucitol and glucitol derivatives, itraconazole, ketoprofen, ketotifen, lacidipine, lansoprazole, levodopa, levomethadone, thyroid hormones, lipoic acid (and derivatives), lisinopril, lisuride, lofepramine, loperamide, loratadine, maprotiline, mebendazole, mebeverine, meclozine, mefenamic acid, mefloquine, meloxicam, mepindolol, meprobamate, mesalazine, mesuximide, metamizole, metformin, methylphenidate, metixene, metoprolol, metronidazole, mianserin, miconazole, minoxidil, misoprostol, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, novamine sulfone, noscapine, nystatin, olanzapine, olsalazine, omeprazole, omoconazole, oxaceprol, oxiconazole, oxymetazoline, pantoprazole, paracetamol (acetaminophen), paroxetine, penciclovir, pentazocine, pentifylline, pentoxifylline, perphenazine, pethidine, plant extracts, phenazone, pheniramine, barbituric acid derivatives, phenylbutazone, pimozide, pindolol, piperazine, piracetam, pirenzepine, piribedil, piroxicam, pramipexole, pravastatin, prazosin, procaine, promazine, propiverine, propranolol, propyphenazone, protionamide, proxyphylline, quetiapine, quinapril, quinaprilat, ramipril, ranitidine, reproterol, reserpine, ribavirin, risperidone, ritonavir, ropinirole, roxatidine, ruscogenin, rutoside (and derivatives), sabadilla, salbutamol, salmeterol, scopolamine, selegiline, sertaconazole, sertindole, sertralion, silicates, simvastatin, sitosterol, sotalol, spaglumic acid, spirapril, spironolactone, stavudine, streptomycin, sucralfate, sufentanil, sulfasalazine, sulpiride, sultiam, sumatriptan, suxamethonium chloride, tacrine, tacrolimus, taliolol, taurolidine, temazepam, tenoxicam, terazosin, terbinafine, terbutaline, terfenadine, terlipressin, tertatolol, teryzoline, theobromine, butizine, thiamazole, phenothiazines, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, tramadol, tramazoline, trandolapril, tranylcypromine, trapidil, trazodone, triamcinolone derivatives, triamterene, trifluperidol, trifluridine, trimipramine, tripelennamine, triprolidine, trifosfamide, tromantadine trometamol, tropalpin, troxerutine, tulobuterol, tyramine, tyrothricin, urapidil, valaciclovir, valproic acid, vancomycin, vecuronium chloride, Viagra, venlafaxine, verapamil, vidarabine, vigabatrin, viloazine, vincamine, vinpocetine, viquidil, warfarin, xantinol nicotinate, xipamide, zafirlukast, zalcitabine, zidovudine, zolmitriptan, zolpidem, zoplicone, zotipine, amphotericin B, caspofungin, voriconazole, resveratrol, PARP-1 inhibitors (including imidazoquinolinone, imidazpyridine, and isoquinolindione, tissue plasminogen activator (tPA), melagatran, lanoteplase, reteplase, staphylokinase, streptokinase, tenecteplase, urokinase, abciximab (ReoPro), eptifibatide, tirofiban, prasugrel, clopidogrel, dipyridamole, cilostazol, VEGF, heparan sulfate, chondroitin sulfate, elongated "RGD" peptide binding domain, CD34 antibodies, cerivastatin, etorvastatin, losartan, valartan, erythropoietin, rosiglitazone, pioglitazone, mutant protein Apo A1 Milano, adiponectin, (NOS) gene therapy, glucagon-like peptide 1, atorvastatin, and atrial natriuretic peptide (ANP), lidocaine, tetracaine, dibucaine, hyssop, ginger, turmeric, Amica montana, helenalin, cannabichromene, rofecoxib, hyaluronidase, and salts, derivatives, isomers, racemates, diastereoisomers, prodrugs, hydrate, ester, or analogs thereof.

For example, coatings on medical devices can include drugs used in time-release drug applications. Proteins may be coated according to these methods and coatings described herein may comprise proteins. Peptides may be coated according to these methods and coatings described herein may comprise peptides.

In exemplary tests of the coating process, coating particles were generated by expansion of a near-critical or a supercritical solution prepared using a hydrofluorcarbon solvent, (e.g., fluoropropane R-236ea, Dyneon, Oakdale, Minn., USA) that further contained a biosorbable polymer used in biomedical applications [e.g., a 50:50 poly(DL-lactide-co-glycolide)] (Catalog No. B6010-2P), available commercially (LACTEL® Absorbable Polymers, a division of Durect, Corp., Pelham, Ala., USA). The supercritical solution was expanded and delivered through the expansion nozzle (FIG. 3) at ambient (i.e., STP) conditions.

Coatings—Single Layer and Multi-Layer

Provided herein is a coating on a surface of a substrate produced by any of the methods described herein. Provided herein is a coating on a surface of a substrate produced by any of the systems described herein.

In addition to single layer films, multi-layer films can also be produced by in some embodiments, e.g., by depositing coating particles made of various materials in a serial or sequential fashion to a selected substrate, e.g., a medical device. For example, in one process, coating particles comprising various single materials (e.g., A, B, C) can form multilayer films of the form A-B-C, including combinations of these layers (e.g., A-B-A-B-C, A-B-C-A-B-C, C-B-A-A-B-C), and various multiples of these film combinations. In other processes, multi-layer films can be prepared, e.g., by depositing coating particles that include more than one material, e.g., a drug (D) and a polymer (P) carrier in a single particle of the form (DP). No limitations are intended. In exemplary tests, 3-layer films and 5-layer films were prepared that included a polymer (P) and a Drug (D), producing films of the form P-D-P and P-D-P-D-P. Films can be formed by depositing the coating particles for each layer sequentially, and then sintering. Alternatively, coating particles for any one layer can be deposited, followed by a sintering step to form the multi-layer film. Tests showed film quality is essentially identical.

Controlling Coating Thickness

Thickness and coating materials are principal parameters for producing coatings suitable, e.g., for medical applications. Film thickness on a substrate is controlled by factors including, but not limited to, e.g., expansion solution concentration, delivery pressure, exposure times, and deposition cycles that deposits coating particles to the substrate. Coating thickness is further controlled such that biosorption of the polymer, drug, and/or other materials delivered in the coating to the substrate is suitable for the intended application. Thickness of any one e-RESS film layer on a substrate may be selected in the range from about 0.1 μm to about 100 μm. For biomedical applications and devices, individual e-RESS film layers may be selected in the range from about 5 μm to about 10 μm. Because thickness will depend on the intended application, no limitations are intended by the exemplary or noted ranges. Quality of the coatings can be inspected, e.g., spectroscopically.

Quantity of Coating Solutes Delivered

Total weight of solutes delivered through the expansion nozzle during the coating process is given by Equation [4], as follows:

$$\text{Total Wt. Delivered(g)} = \text{Flow}\left(\frac{\text{mL}}{\text{sec}}\right)\times \textit{Conc.}\ \text{in}\ \textit{SCF Soln}\left(\frac{\text{g}}{\text{mL}}\right)\times\text{Time (sec)} \quad [4]$$

Weight of coating solute deposited onto a selected substrate (e.g., a medical stent) is given by Equation [5], as follows:

$$\text{Total Wt. Collected (g)}=\Sigma_1^N[(\text{Wt (after)}-\text{Wt (before)}] \quad [5]$$

In Equation [5], (N) is the number of substrates or stents. The coating weight is represented as the total weight of solute (e.g., polymer, drug, etc.) collected on all substrates (e.g., stents) present in the deposition vessel divided by the total number of substrates (e.g., stents).

Coating Efficiency

"Coating efficiency" as used herein means the quantity of coating particles that are actually incorporated into a coating deposited on a surface of a substrate (e.g., stent). The coating efficiency normalized per surface is given by Equation [6], as follows:

$$\text{Coating Efficiency per Stent (Normalized)} = \frac{\left(\frac{\text{Total Wt. Collected}}{\text{No. of Stents}}\right)}{\left(\frac{\text{Total Wt. Delivered}}{\text{12 Stents}}\right)}\times 100\% \quad [6]$$

A coating efficiency of 100% represents the condition in which all of the coating particles emitted in the RESS expansion are collected and incorporated into the coating on the substrate.

In three exemplary tests involving three (3) stents coated using the auxiliary emitter, coating efficiency values were: 45.6%, 39.6%, and 38.4%, respectively. Two tests without use of the auxiliary emitter gave coating efficiency values of 7.1% and 8.4%, respectively. Results demonstrate that certain embodiments enhance the charge and the collection (deposition) efficiency of the coating particles as compared to similar processes without the auxiliary emitter (i.e., charged ions). In particular, coating efficiencies with the auxiliary emitter are on the order of ~45% presently, representing a 5-fold enhancement over conventional RESS coatings performed under otherwise comparable conditions without the auxiliary emitter. Results further show that e-RESS coatings can be effectively sintered (e.g., using heat sintering and/or gas/solvent sintering) to form dense, thermally stable single and multilayer films.

Coating Density

Particles that form coatings on a substrate can achieve a maximum density defined by particle close packing theory. For spherical particles of uniform size, this theoretical maximum is about 60 volume %. e-RESS coating particles prepared from various materials described herein (e.g., polymers and drugs) can be applied as single layers or as multiple layers at selected coating densities, e.g., on medical devices. Coatings applied in conjunction with some embodiments can be selected at coating densities of from about 1 volume % to about 60 volume %. Factors that define coating densities for selected applications include, but are not limited to, e.g., time of deposition, rate of deposition, solute concentrations, solvent ratios, number of coating layers, and combinations of these factors. In various embodiments, coatings composed of biosorbable polymers have been shown to produce coatings with selectable coating densities. In one exemplary test, a coating that included poly(lactic-co-glycolic acid, or PLGA) polymer at a solute concentration of 1 mg/mL was used to generate a coating density greater than about 5 volume % on a stent device, but density is not limited thereto. These coated polymers have also been shown to effectively release these drugs at the various coating densities selected. Coatings applied in some embodiments show an improvement in weight gain, an enhanced coating density, and a low dendricity.

Dendricity Rating

Dendricity (or dendricity rating) is a qualitative measure that assesses the quality of a particular coating deposited in some embodiments on a scale of 1 (low dendricity) to 10 (high dendricity). A high dendricity rating is given to coatings that have a fuzzy or shaggy appearance under magnification, include a large quantity of fibers or particle accumulations on the surface, and have a poor coating density (<1 volume %). A low dendricity rating is given to coatings that are uniform, smooth, and have a high coating density (>1 volume %). Low dendricity e-RESS coatings produce more uniform and dense layers, which are advantageous for selected applications, including, e.g., coating of medical devices for use in biomedical applications. FIG. 6 is an optical micrograph that shows a stent 34 (~160× magnification) with an enhanced e-RESS (PLGA) coating that is non-dendritic that was applied in conjunction with the auxiliary emitter of the invention described herein. In the figure, the coating on stent 34 is uniform, has a high coating density (~10 volume %). This coating contrasts with the dendritic coating shown previously in FIG. 1 with a low coating density (~0.01 volume %).

While an exemplary embodiment has been shown and described, it will be apparent to those skilled in the art that many changes and modifications may be made without departing from the invention in its true scope and broader aspects. The appended claims are therefore intended to cover all such changes and modifications as fall within the spirit and scope of the invention.

The following examples will promote a further understanding of the invention and various aspects thereof.

Example 1

Coating Tests

Coating efficiency tests were conducted in a deposition vessel (e.g., 8-liter glass bell jar) centered over a base platform equipped with an auxiliary emitter and e-RESS expansion nozzle assembly. The invention auxiliary emitter was positioned at the top of, and external to, the deposition vessel. The auxiliary emitter was configured with a $1^{st}$ auxiliary electrode consisting of a central stainless steel rod (⅛-inch diameter) having a tapered tip that was grounded, and a ring collector (⅛-inch copper) as a $2^{nd}$ auxiliary electrode. Charged ions from the auxiliary emitter were carried in (e.g., $N_2$) carrier gas into the deposition vessel. An exemplary flow rate of pure carrier gas (e.g., $N_2$) through the auxiliary emitter was 4.5 L/min. The auxiliary emitter was operated at an exemplary current of 1 μA under current/feedback control. The e-RESS expansion nozzle assembly included a metal sheath, as a first e-RESS electrode composed of a length (~4 inches) of stainless steel tubing (¼-inch O.D.) that surrounded an equal length of tubing (1/16-inch O.D.×0.0025-inch I.D.) composed of poly-ethyl-ethyl-ketone (PEEK) (IDEX, Northbrook, Ill., USA). The first e-RESS electrode was grounded. Three (3) stents, acting collectively as a $2^{nd}$ e-RESS electrode, were mounted on twisted wire stent holders at positions 1, 4, and 9 of a 12-position, non-rotating stage equidistant from the e-RESS expansion nozzle. Wire stent holders were capped at the terminal ends with plastic beads to prevent coronal discharge. A voltage of −15 kV was applied to the stents. The vessel was purged with dry ($N_2$) gas for >20 minutes to give a relative humidity below about 0.1%. A 50:50 Poly(DL-lactide-co-glycolide) bioabsorbable polymer (Catalog No. B6010-2P) available commercially (LACTEL® Absorbable Polymers, a division of Durectel, Corp., Pelham, Ala., U.S.A.) was prepared in a fluorohydrocarbon solvent (e.g., R-236ea [M.W. 152.04 g/moL], Dyneon, Oaksdale, Minn., USA) at a concentration of 1 mg/mL. The solvent solution was delivered through the expansion nozzle at a pressure of 5500 psi and an initial temperature of 150° C. Polymer expansion solution prepared in fluoropropane solvent (i.e., R-236ea) was sprayed at a pump flow rate of 7.5 mL/min for a time of ~90 seconds. Flow rate of R-236ea gas [Pump flow rate (ml/min)×ρ(g/ml)×(1/MW (g/mol))×STP (Umol)=L/min] was 1.7 L/min. Percentage of fluoropropane gas (R-236ea, Dyneon, Oakdale, Minn., USA) and $N_2$ gas in the enclosure vessel was: 27% [(1.7/(1.7+4.5))×100=27%] and 73%, respectively. Moles of each gas in the enclosure vessel were 0.096 moles (R-236ea) and 0.26 moles (N2), respectively. Mole fractions for each gas in the enclosure vessel were 0.27 (R-236ea) and 0.73 ($N_2$), respectively. Viscosity (at STP) of the gas mixture (R-236ea and $N_2$) in the enclosure vessel at the end of the experiment was calculated from the Chapman-Enskog relation to be (minus) −14.5 μPa·sec.

Weight gains on each of the three stents from deposited coatings were: 380 μg, 430 μg, and 450 μg, respectively. In a second test, polymer expansion solution was sprayed for a time of ~60 seconds at a flow rate of 7.4 mL/min. Charged ions from the auxiliary emitter were carried into the deposition vessel using ($N_2$) gas at a flow rate of 6.5 L/min. Weight gains for each of the three stents from deposited coatings were: 232 μg, 252 μg, and 262 μg, respectively. In tests 1 and 2, moderate-to-heavy coatings were deposited to the stents. Test results showed the first stent had a lower coating weight that was attributed to: location on the mounting stage relative to the expansion nozzle, and lack of rotation of both the stent and stage. Dendricity values of from 1 to 2 were typical, as assessed by the minimal quantity of dendrite fibers observed (e.g., 50× magnification) on the surface. Collection efficiencies for these tests were 45.4% and 40.3%, respectively.

Example 2

Coatings Deposited Absent the Auxiliary Emitter

A test was performed as in Example 1 without use of the auxiliary emitter. Weight gains from deposited coatings for each of three stents were: 22 μg, 40 μg, and 42 μg, respectively. Coating efficiency for the test was 5.0%. Results showed coatings on the stents were light, non-uniform, and dendritic. Coatings were heaviest at the upper end of the stents and had a dendricity rating of ~7, on average. Heavier coatings were observed near the top of the stents. Lighter coatings were observed at the mid-to-lower end of the stents, with some amount of the metal stent clearly visible through the coatings.

Example 3

Effect of Increasing Emitter Current on Deposited Polymer Weight/Structure

A dramatic effect is observed in weight gains for applied coatings at the initial onset of auxiliary emitter current. A gradual increase in weight gains occurs with increasing current between about 0.1 μA and 1 μA. Thereafter, a gradual decrease in weight gains occurs with change in auxiliary emitter current between about 1 μA and 5 μA, most likely due to a saturation of charge transferred to particles by the auxiliary emitter.

CONCLUSIONS

Use of an auxiliary emitter has demonstrated improvement in quality (e.g., dendricity, density, and weight) of electrostatically collected (deposited) coating particles on substrate surfaces. The auxiliary emitter has particular application to e-RESS coating processes, which coatings previous to the invention have been susceptible to formation of dendritic features.

What is claimed is:

1. A method for forming a coating on a surface of a substrate, comprising:

providing a substrate;

establishing an electric field between said substrate and a counter electrode;

producing coating particles suspended in a gaseous phase of an expanded near-critical or supercritical fluid released from an expansion nozzle having a first average electric potential; and contacting said coating particles with a stream of charged ions from an auxiliary emitter at a second average electric potential in an inert carrier gas to increase the charge differential between said coating particles and said substrate, wherein said coating particles impact said substrate to form a coating on the surface of the substrate.

2. The method of claim 1, wherein the coating particles have a first velocity upon release of the coating particles from the expansion nozzle that is less than a second velocity of the coating particles when said coating particles impact said substrate.

3. The method of claim 1, wherein attraction of the coating particles to the substrate is increased as compared to attraction of the coating particles to the substrate in a system without the auxiliary emitter.

4. The method of claim 1, wherein the first average electric potential is different than the second average electric potential.

5. The method of claim 1, wherein an absolute value of the first average electric potential is less than an absolute value of the second average electric potential, and wherein a polarity of the charged ions is the same as a polarity of the coating particles.

6. The method of claim 1, wherein said coating particles have a size between about 0.01 micrometers and about 10 micrometers.

7. The method of claim 1, wherein said substrate has a negative polarity and an enhanced charge of said coating particles following the contacting step is a positive charge; or wherein said substrate has a positive polarity and an enhanced charge of said coating particles following the contacting step is a negative charge.

8. The method of claim 1, wherein the contacting step comprises forming a positive corona or forming a negative corona positioned between the expansion nozzle and said substrate.

9. The method of claim 1, wherein the contacting step comprises forming a positive corona or forming a negative corona positioned between the auxiliary emitter and said substrate.

10. The method of claim 1, wherein the coating has a density on said surface from about 1 volume % to about 60 volume %.

11. The method of claim 1, wherein said coating particles comprises at least one of: a polymer, a drug, a biosorbable material, a protein, a peptide, or a combination thereof.

12. The method of claim 1, wherein said coating particles comprises at least one of: polylactic acid (PLA); poly(lactic-co-glycolic acid) (PLGA); polycaprolactone (poly(e-caprolactone)) (PCL), polyglycolide (PG) or (PGA), poly-3-hydroxybutyrate; LPLA poly(l-lactide), DLPLA poly(dl-lactide), PDO poly(dioxolane), PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid) and blends, combinations, homopolymers, condensation polymers, alternating, block, dendritic, crosslinked, or copolymers thereof.

13. The method of claim 1, wherein said coating particles comprise at least one of: polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-byta-diene, and blends, combinations, homopolymers, condensation polymers, alternating, block, dendritic, crosslinked, or copolymers thereof.

14. The method of claim 1, wherein said coating particles include a drug comprising one or more of: rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxyethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)rapamycin(zotarolimus), salts, derivatives, isomers, racemates, diastereoisomers, prodrugs, hydrate, ester, or analogs thereof.

15. The method of claim 1, wherein said coating on said substrate comprises polylactoglycolic acid (PLGA) at a density greater than 5 volume %.

16. The method of claim 2, wherein the second velocity is in the range from about 0.1 cm/sec to about 100 cm/sec.

17. The method of claim 1, further including the step of sintering said coating at a temperature in the range from about 25° C. to about 150° C. to form a dense, thermally stable film on said surface of said substrate.

18. The method of claim 1, further including the step of sintering said coating in the presence of a solvent gas to form said dense, thermally stable film on said surface of said substrate.

19. The method of claim 1, wherein said producing and said contacting steps, at least, are repeated to form a multilayer film.

20. The method of claim 1, wherein said substrate is at least a portion of a medical implant.

21. The method of claim 1, wherein said substrate is an interventional device.

22. The method of claim 1, wherein said substrate is a diagnostic device.

23. The method of claim 1, wherein said substrate is a surgical tool.

24. The method of claim 1, wherein said substrate is a stent.

25. The method of claim 1, wherein said substrate is a medical balloon.

26. The method of claim 1, wherein the coating is nondendritic as compared to a baseline average coating thickness.

27. The method of claim 26, wherein no coating extends more than 0.5 microns from the baseline average coating thickness.

28. The method of claim 26, wherein no coating extends more than 1 micron from the baseline average coating thickness.

29. The method of claim 1, wherein the coating is nondendritic such that there is no surface irregularity of the coating greater than 0.5 microns.

30. The method of claim 1, wherein the coating is nondendritic such that there is no surface irregularity of the coating greater than 1 micron.

31. The method of claim 1, wherein the coating is nondendritic such that there is no surface irregularity of the coating greater than 2 microns following sintering of the coated substrate.

32. The method of claim 1, wherein the coating is nondendritic such that there is no surface irregularity of the coating greater than 3 microns following sintering of the coated substrate.

* * * * *